(12) United States Patent
Zeller et al.

(10) Patent No.: US 11,152,099 B2
(45) Date of Patent: Oct. 19, 2021

(54) SYSTEM AND PROCESS FOR MANAGING PARTICIPATION AND PROGRESSION IN HEALTH ENGAGEMENT PROGRAMS

(71) Applicant: Kiio Inc., Madison, WI (US)

(72) Inventors: Lydia J. Zeller, Madison, WI (US); Chad Lindley, Mount Horeb, WI (US); David J. Grandin, Fitchburg, WI (US); Brian Andrew Rossman, Madison, WI (US); Lars James Lervik, Waunakee, WI (US)

(73) Assignee: KIIO Inc., Madison, WI (US)

( * ) Notice: Subject to any disclaimer, the term of this patent is extended or adjusted under 35 U.S.C. 154(b) by 514 days.

(21) Appl. No.: 16/195,658

(22) Filed: Nov. 19, 2018

(65) Prior Publication Data

US 2019/0214125 A1  Jul. 11, 2019

Related U.S. Application Data

(60) Provisional application No. 62/587,589, filed on Nov. 17, 2017.

(51) Int. Cl.
*G16H 20/30* (2018.01)
*G16H 80/00* (2018.01)
(Continued)

(52) U.S. Cl.
CPC ............. *G16H 20/30* (2018.01); *G16H 10/20* (2018.01); *G16H 40/67* (2018.01); *G16H 50/30* (2018.01); *G16H 80/00* (2018.01)

(58) Field of Classification Search
CPC ........ G16H 50/30; G16H 10/20; G16H 20/30; G16H 40/67; G16H 80/00
(Continued)

(56) References Cited

U.S. PATENT DOCUMENTS

| | | | | |
|---|---|---|---|---|
| 2012/0191469 A1* | 7/2012 | Akradi | ................... | G16H 50/30 705/2 |
| 2013/0325500 A1* | 12/2013 | Schoenberg | ........... | G16H 50/30 705/2 |

(Continued)

FOREIGN PATENT DOCUMENTS

| WO | WO-2013192071 A1 * | 12/2013 | ........... A61B 5/0022 |
|---|---|---|---|
| WO | WO-2018170498 A1 * | 9/2018 | ............. G16H 20/10 |

OTHER PUBLICATIONS

Taki et al., Assessing User Engagement of an mHealth Intervention: Development and Implementation of the Growing Healthy App Engagement Index, JMIR Mhealth and Uhealth, Jun. 29, 2017; vol. 5, No. 6, e89, doi: 10.2196/mhealth.7236 (Year: 2017).*
Nitsch et al., A Guided Online and Mobile Self-Help Program for Individuals With Eating Disorders: An Iterative Engagement and Usability Study, Journal of Medical Internet Research, Jan. 11, 2016; vol. 18, No. 1, e7, doi: 10.2196/jmir.4972 (Year: 2016).*
Barello et al., eHealth for Patient Engagement: A Systematic Review, Frontiers In Psychology, Jan. 8, 2016, vol. 6, Article 2013, pp. 1-13, doi=10.3389/fpsyg.2015.02013 (Year: 2016).*

*Primary Examiner* — Joy Chng
(74) *Attorney, Agent, or Firm* — Husch Blackwell LLP

(57) ABSTRACT

A computerized process for managing member participation and progression in a health engagement program including the steps of automatically validating eligible members, queuing for manual review and validation, members not automatically validated, and providing an interactive portal to enable an administrator to manually validate. Also, gathering with the assistance of a communication device in communication with a server, member screening information that includes access to equipment required for the health engagement program, and at least one medical factor associated with each member's health history. Further, stratifying, with the assistance of an application program in communication with the server, each of the validated members into risk categories based on the screening information gathered, and determining whether each validated member is appropriate for and suitable to continue with the health (Continued)

engagement program, and flagging, if deemed appropriate, each of the validated members indicating conditions for participation by analyzing the screening information.

41 Claims, 22 Drawing Sheets

(51) Int. Cl.
*G16H 50/30* (2018.01)
*G16H 10/20* (2018.01)
*G16H 40/67* (2018.01)

(58) Field of Classification Search
USPC .......................................................... 705/2–3
See application file for complete search history.

(56) References Cited

U.S. PATENT DOCUMENTS

2016/0074707 A1* 3/2016 Thorpe .............. G09B 19/0076
 434/127
2017/0301258 A1* 10/2017 Ram ........................ G09B 5/02
2017/0323582 A1* 11/2017 Nusbaum ................ G09B 19/00

* cited by examiner

LOW BACK PAIN PROGRAM

SCREENING — PROGRESS INDICATOR

PROGRAM FAQS

HAVE YOU HAD A VISIT IN YOUR PRIMARY CARE CLINIC WITHIN THE LAST YEAR?  ○ YES  ○ NO

DO YOU HAVE A SMARTPHONE OR TABLET (APPLE OR ANDROID) YOU CAN USE TO ACCESS THE MOBILE APP USED IN THIS PROGRAM?  ○ YES  ○ NO

DO YOU HAVE AN ACTIVE ELECTRONIC HEALTH RECORDS ACCOUNT?  ○ YES  ○ NO

PLEASE CHECK PROVIDER LOCATIONS YOU PREFER TO USE - CHECK AS MANY AS APPLY

○ DOWNTOWN
   621 WACKER DR., CHICAGO
○ WEST SUBURBS
   6630 MAIN ST..., NAPERVILLE
○ SOUTHSIDE
   1050 EAST BROADWAY, JOILET
○ NORTH SUBURBS
   4602 EASTPARK BLVD,

LOW BACK PAIN PROGRAM

PROGRAM FAQS

SCREENING

| | YES | NO |
|---|---|---|
| 1. ARE YOU OLDER THAN AGE 50 AND HAVE A HISTORY OF HIGH BLOOD PRESSURE? | ○ | ○ |
| IF YES, HAVE YOU SEEN YOUR PRIMARY CARE PRACTITIONER IN THE PAST YEAR? | ○ | ○ |
| IF YES, BLOOD PRESSURE UNDER CONTROL (LESS THAN 140/90)? | ○ | ○ |
| 2. DO YOU HAVE A PAST DIAGNOSIS OF CANCER? | ○ | ○ |
| IF YES, ARE YOU CURRENTLY BEING TREATED FOR CANCER? | ○ | ○ |
| 3. HAVE YOU HAD A SIGNIFICANT, ACUTE FLARE-UP OF YOUR BACK OR LEG PAIN IN THE PAST 2 WEEKS? | ○ | ○ |
| 4. HAVE YOU NOTICED ON UNEXPLAINED WEIGHT LOSS RECENTLY OR IN THE PAST 3 MONTHS (LOSING 10 POUNDS ARE MORE WITHOUT A CHANGE IN YOUR DIET OR EXERCISE HABITS)? | ○ | ○ |
| 5. DO YOU HAVE DIFFICULTY WITH STARTING/STOPPING FLOW OF URINE OR FECES? | ○ | ○ |
| 6. IS YOUR PAIN WORSE AT NIGHT (WHILE RESTING)? | ○ | ○ |
| 7. DO YOU HAVE LEG PAIN/NUMBNESS OR TINGLING THAT IS MORE BOTHERSOME THAN YOUR BACK PAIN? | ○ | ○ |
| 8. DOES YOUR LOW BACK PAIN WRAP AROUND YOUR TRUNK IN A WAISTBAND- LIKE PATTERN? | ○ | ○ |

LOW BACK PAIN DASHBOARD

DASHBOARD | FAQ | REPORTS

REPORT: YELLOW FLAG DISPOSITION

START DATE ▼ | END DATE ▼ | RUN

🔍 NAME, DOB, NOTE KEYWORD

| USER ▼ | TRIGGER DATE ▼ | TRIGGER ▼ | LAST ▼ | FIRST ▼ | STAGE ▼ | RISK ▼ | PT? ▼ | DISP DATE ▼ | DISPOSITION ▼ |
|---|---|---|---|---|---|---|---|---|---|
| LW | 07/01/201 | INACTIVITY | MEMBER | JANE | SCREENING | | N | | OPEN |
| TT | 07/05/201 | REQUEST | MEMBER | ANNA | LEVEL 1 | M | Y | 07/05/201 | INACTIVATED |
| TT | 07/05/201 | INACTIVITY | MEMBER | JOE | LEVEL 2 | L | Y | 07/05/201 | RESOLVED |
| TT | 07/05/201 | COACH | MEMBER | JOE | LEVEL 2 | L | N | 07/05/201 | INELIGIBLE |
| TT | 07/05/201 | COACH | MEMBER | JOE | LEVEL 2 | L | N | 07/05/201 | REFERRED TO |

EXPORT TO CSV

SYSTEM AND PROCESS FOR MANAGING PARTICIPATION AND PROGRESSION IN HEALTH ENGAGEMENT PROGRAMS

CROSS-REFERENCE TO RELATED APPLICATION

This application claims benefit to U.S. Provisional Pat. Appl. No. 62/587,589, filed on Nov. 17, 2017, the disclosure of which is incorporated herein by reference in entirety for all purposes.

FIELD OF THE INVENTION

The system and process relate generally to the field of health engagement programs. More particularly, the system and process relate to managing participation and progression in health engagement programs.

BACKGROUND

Health care management has become increasingly important due to the dramatic rise in numerous health issues, such as low back pain for example. Low back pain is a fixture on the World Health Organization's top priority disease list due to its prevalence, recurrence, cost, and impact on work performance, disability rates, and quality of life. In the U.S., median annual prevalence is 37%, with nearly 29%° of the adult population suffering low back pain in the past three months. In addition, lifetime prevalence is estimated at 70%, and 50% of sufferers experience a recurrence within 12 months.

Annual U.S. costs currently exceed $100 billion and the condition is routinely in the top three medical cost drivers for healthcare insurance companies. In addition to direct medical costs, low back pain has a significant impact on employment costs. Low back pain is the leading cause of lost work days and activity limitation. It is responsible for approximately 40% of all missed work days and an estimated 30% of sufferers file for disability.

Currently, a majority of low back pain sufferers seek care from their primary care physician. Unfortunately, studies show that most general practitioners do not appropriately triage patients by identifying individuals that require specialized treatment over those likely to recover with appropriate self-managed care. Compounding the problem, most general practitioners lack specific training in appropriate exercises and education for the various types of low back pain. The result being a significant percentage of members are directed to additional diagnostics and services that may be unnecessary. Referrals to specialists, prescription rates for opioids, lumbar spine MRI imaging, epidural steroid injections, and lumbar fusion and disc replacement surgeries have climbed significantly over the last twenty years with a corresponding rise in health care costs. Of greater concern is the discordance between these escalating treatments and concurrent increases in disability and chronicity. Specifically, rather than declining in response to increased treatment, self-reported functional limitations and disability rates have increased.

SUMMARY

In at least some embodiments, a system and process for managing participation and progression in a health engagement program is disclosed that includes an automated registration, validation, screening, triage, and multi-modal care delivery program for members within health engagement programs. The automated process and system collect both subjective and objective data for processing by computer analyses. The results are used to triage members into corresponding risk categories and assign appropriate care delivery protocols—including automated disbursement of instructions and exercise routine progressions, educational materials, or referral to appropriate medical professionals for treatment.

In at least some embodiments, a system and process for managing participation and progression in a health engagement program is disclosed that includes automated registration, validation, screening, triage, and multi-modal, multi-level care delivery for members in health engagement programs that reduces costs and improves both quality of and access to care. The invention improves efficiency and efficacy through direct collection of data and automated interaction with members, which data and interaction points are utilized by a computerized, analysis-based screening and progression system capable of making consistent and appropriate triage and progression decisions without the need for direct involvement of medical personnel. The positive results of this process have been demonstrated through pilots of one embodiment of the system configured for low back pain sufferers.

In at least some embodiments, a system for managing participation and progression in a health engagement program is disclosed that includes: a server having a processor, an operating system, a storage device, and an application program that includes a registration application and a screening application; a network in communication with the server, one or more databases, and a first communication device; wherein the registration application and screening application are both accessible by the first communication device via one or more portals over the network, and wherein the registration application communicates a plurality of registration-based queries to the first communication device and receives registration-based query responses inputted to the first communication device by a member; wherein the received registration-based query responses include member information that is compared by the registration application to a listing of eligible member information on the one or more databases to determine participation eligibility of the member in the health engagement program, and wherein confirmation of eligibility generates the communication of a plurality of screening-based queries to the first communication device by the screening application, and wherein non-confirmation of eligibility by the registration application initiates a manual validation request communicated to a second communication device operable by an administrator, wherein receipt by the registration application of a manual validation by an administrator generates communication of the plurality of screening-based queries to the first communication device by the screening application; wherein screening-based query responses to the screening-based queries are analyzed by the application program to select one of a plurality of exercise tracks and one of a plurality of risk categories associated with the health engagement program; wherein an associated exercise routine is selected by the application program based on the screening-based query responses, the selected exercise track, and the selected risk category, and communicated to the first communication device by the application program for viewing by the member; wherein exercise survey feedback is requested from the member upon completion of an exercise from the exercise routine; wherein routine survey feedback is requested from the member upon substantial completion of all exercises from the exercise routine; wherein program survey feedback is requested from the member; and wherein the application program executes a progression analysis to determine if the member is to one of: i) be advanced to a subsequent level to receive access to an additional associated exercise routine; ii) remain at the current level and repeat the current exercise routine; or iii) be stopped from further participation.

In at least some embodiments, a computerized process for managing member participation and progression in a health engagement program is disclosed that includes: communicating over a network, a plurality of registration-based queries from a server to a first communication device; receiving from the first communication device, registration-based query responses inputted by a member using the first communication device, wherein the registration-based query responses include member identification data; determining health engagement program participation eligibility of the member by comparing at least a portion of the member identification data with a list of eligible member identification data stored in one or more databases in communication with the server, wherein confirmation of member eligibility initiates the communication of a plurality of screening-based queries to the first communication device, and wherein a lack of confirmation of eligibility during the comparison initiates communication to a second communication device, operable by an administrator, of a request for a manual validation, and wherein receipt of the manual validation by the administrator the plurality of screening-based queries is communicated to the first communication device; receiving screening-based query responses from the first communication device; analyzing the screening-based query responses and selecting one of a plurality of exercise tracks and one of a plurality of risk categories associated with the health engagement program; selecting an associated exercise routine based on the screening-based query responses, the selected exercise track, and the selected risk category; communicating the exercise routine to the first communication device for viewing by the member thereon; receiving a selection by the member to view the exercise routine; upon completion of the exercise routine, communicating a request to the first communication device for the member to provide survey feedback, wherein the survey feedback includes a plurality of survey questions presented to the member; and analyzing the responses to the survey feedback and determining if the member shall, i) progress to a subsequent level in the program, thereby receiving access to a new exercise routine, ii) remain at the current level, thereby repeating the current exercise routine, or iii) be stopped from further participation by revocation of the member's access to the exercise routine.

In at least some embodiments, a computerized process for managing member participation and progression in a health engagement program is disclosed that includes: requesting and receiving member identification information from a member communicated between a server and a first communication device operated by the member; comparing at the server, the member identification information to a list of known eligible members in one or more databases and automatically validating eligible members to participate in the health engagement program if provided on the list, and queuing members not on the list for manual review and validation; providing an interactive portal in communication with the server to enable an administrator using a second communication device to manually validate or invalidate queued members not on the list; after validation, requesting and receiving a plurality of screening-based query responses from the member, wherein the screening-based query responses are directed to a medical condition experienced by the member, activities that aggravate the condition, and the member's medical history; analyzing the screening-based query responses and stratifying the member into a selected exercise track and risk category based on the disclosed condition, activities that aggravate the condition, and the member's medical history; selecting an associated exercise routine from a plurality of exercise routines based on the screening-based query responses, the selected exercise track, and the selected risk category; and providing the member access to view the exercise routine through a mobile application or web browser operating on the first communication device.

In at least some embodiments, a computerized process for managing member participation and progression in a health engagement program is disclosed that includes the steps of: for a plurality of members, gathering member identification information with the assistance of a plurality of communication devices and a server; for the plurality of members, comparing the member identification information to a list of eligible members in one or more databases to automatically validate eligible members found in the list and allow them to continue as validated members in the health engagement program; queuing for manual review and validation, the plurality of members not automatically validated, and providing an interactive portal to enable an administrator to manually validate for participation in the health engagement program, wherein the interactive portal is in communication with the server; for the validated members, gathering with the assistance of a communication device in communication with the server, member screening information that includes access to equipment required for the health engagement program, and at least one medical factor associated with each member's health history, taken from a group consisting of (a) type of condition, (b) relevant comorbidities (c) current pain level, (d) highest level of pain over a certain period, (e) activities that aggravate the condition, and (f) activities of daily living affected by the condition; stratifying, with the assistance of an application program in communication with the server, each of the validated members into risk categories based on the screening information gathered; and with the assistance of the application program, determining whether each validated member is appropriate for and suitable to continue with the health engagement program, and flagging, if deemed appropriate, each of the validated members indicating conditions for participation by analyzing the screening information gathered.

A program developed from at least one embodiment of the present invention has been tested in a group of individuals suffering from chronic low back pain (LBP). The following data are specific to those individuals (n=71) who completed screening, were appropriate for the digital care program, and who completed five or more exercise routines using the mobile application. Data were extracted from a proprietary central database for this group, including gender, age, and pain at baseline and at each subsequent exercise routine using the 11 point numeric rating scale (NRS, 0-10). The primary statistical analysis evaluated the mean difference in self-rated pain from baseline to the last recorded pain report with a paired t-test. Additionally, the group of 71 was split by symptom severity into a high (5 or greater) and low (4 or less) group. Mean differences from baseline were calculated for each severity group and a "responder" analysis was completed using 30% improvement in NRS as the threshold for a positive response.

There were 45 females and 26 males in the participant group with an average age of 55 years (range 22-77). The median number of exercise routines completed was 16 (range 5-81) over a median of 37 days (range 4-142). The average pain at baseline (on a scale of 0-10) was 4.3 (SD=2.0) and at last available interaction 2.2 (SD=1.7). The mean difference was 2.1 ([95% CI 1.7-2.6], $p<0.01$, Cohen's $d=1.1$). This is an average pain reduction of 50%. When split by symptom severity, the "high" severity group (n=31) averaged 6.2 (SD=1.0) at baseline and 3.10 (SD=1.8) at last interaction, which is a symptom reduction of 52%. The "low" severity group (n=40) averaged 2.8 (SD=1.0) at baseline and 1.5 (SD=1.3) at last interaction, resulting in a symptom reduction of 45%. In the high severity group, 23 individuals exceeded the 30% improvement threshold, while in the low severity group 26 individuals exceeded this threshold (Odds Ratio=1.54 [95% CI 0.55-4.35]).

The results demonstrate a statistically significant improvement in self-reported LBP from baseline to the last reported interaction for individuals with a minimum of five completed exercise routines. The results are also clinically significant with a large effect size (d=1.1) and average improvement of approximately 50%. This exceeds the published minimum clinically important difference (MCID=30%) and perceived smallest worthwhile effect (20%). Additionally, since average scores are influenced by individuals with extreme values, it is important to include a responder analysis. In this sub-group, 49 of 71 individuals (approximately 70%) met or exceeded the MCID. When the sub-group was analyzed based on severity of symptoms at baseline, small differences were noted. While both groups, on average, exceeded the MCID, the likelihood of an individual surpassing that threshold was approximately 1.5 times greater in the high severity group. The confidence interval includes 1.0 and, thus, this difference may be negligible. This suggests the invention is widely applicable to members with various levels of impairment.

The positive results of this embodiment of the present invention are not limited to reductions in pain for participants. In a later analysis of claims data, after completing the online screening, a total of 515 insurance plan members were eligible to participate in the digital care portion of this embodiment. For analysis purposes, the group was split into two groups: Those individuals who engaged with the program and participated long enough to advance beyond the first level of exercises, now referred to as the "participant group", and those who did not participate long enough to progress beyond the first level, now referred to as the "reference group" (Table 1).

TABLE 1

Demographics

| Group | n | Age, yrs (range) | # Female (%) | Baseline pain* | Medical spend (%)** |
|---|---|---|---|---|---|
| Reference | 454 | 48.8 (20.9-85.1) | 294 (65) | 3.95/10 | 100 |
| Participant | 61 | 53.7 (22.3-74.6) | 40 (66) | 4.02/10 | 99.2 |

*Pain scores based on NRS pain scale
**Medical spend defined as medical claims greater than $0, with a low back pain-related diagnosis code, and excluding pharmacy Data were extracted from the insurer's primary database on service utilization and cross-referenced with the present invention's central database of usage metrics using unique ID numbers. Medical claims data included dollars billed for all claims with a low back pain-related diagnosis code. This was analyzed separately from prescription claims data, for which, dollars billed was not provided.

For all individuals, the date used to define the beginning of the "pre" period was the earliest of the data set, i.e. Jan. 27, 2015. For the participant group, each individual had a unique date on which this embodiment of the present invention was started, so the "pre" period ended with each individual's date of the first interaction with the invention. This date also defined the beginning of the "post" period for each member. As a result, each individual's time spent in the "pre" and "post" periods was unique (average pre=28.95 months, average post=8.16 months). For the reference group, the average start date of the participant group was used to define the end of the "pre" period and the beginning of the "post" period, because these individuals did not sufficiently engage with the invention. The end of the post period for all groups was defined as the last of the data set, i.e. Apr. 1, 2018.

Baseline data were analyzed using t-tests or Chi squared tests to consider any potentially confounding differences present before introduction into the program. These include age, gender, baseline pain, and total medical spending (low back pain-related diagnosis code, excluding pharmacy) per member per month (PMPM), and normalized to 100% for the reference group (Table 1). The total medical spending data were log transformed prior to statistical testing due to a right skewed distribution. The primary outcomes were total medical claim items defined as any service with a billed amount greater than $0 and number of individuals with a filled prescription for both opioid and non-opioid medications. Primary outcomes were analyzed using a Chi squared test to determine group differences in observed and expected events (i.e. claims or individuals with a prescription) for both the pre- and post-time frames ($\alpha=0.05$). Secondary outcomes include percent change in expenditures from the pre- to post-time frame for each group for total LBP-related medical, advanced imaging (MRI/CT), injections, Emergency/Urgent care, and a conglomerate measure of the expenditures for the most frequently provided services (top 10% most frequent services, thought to best reflect spending most directly related to LBP). Secondary outcomes also included an analysis of the percent change in the rate of opioid and non-opioid medication prescriptions (prescriptions filled PMPM). Percent change values were used to protect the confidential nature of the claims data. Finally, odds ratios were calculated to investigate the relative likelihood of individuals in each group having a billed service or filled prescription in both the pre- and post-time frames.

The age difference was small, but statistically significant ($p<0.05$), while gender, pain, and total medical spending did not differ between groups. For the primary analysis, there were no significant differences between groups in the pre-period for the number of claim items ($X^2=0.60$), or the number of individuals with an opioid ($X^2=2.98$), or non-opioid prescription ($X^2=2.00$). In the post period, all primary outcomes were significantly reduced in the participant group compared to the reference group: Total claim items ($X^2=12.05$, $p<0.01$), the number of individuals with a filled prescription for opioids ($X^2=7.3$, $p<0.01$), and the number of individuals with a filled prescription for non-opioids ($X^2=4.8$, $p<0.05$). All percent change values for secondary outcomes are presented in Table 2. Odds ratios are presented in Table 3.

TABLE 2

Secondary outcome percent changes from pre to post time frame.

| Outcome | Reference Group (% reduction)* | Participant Group (% reduction)* |
|---|---|---|
| Expenditures | | |
| Total medical | 33 | 55 |
| Advanced imaging | 0 | 81 |
| Injection | +29 | +40 |
| ED/Urgent care | +81 | 100 |
| Most frequent services | 4 | 27 |
| Prescription rates | | |
| Opioid | 2 | 78 |
| Non-opioid | +22 | 33 |
| Pain reduction | N/A/26** | 45 |

*+ indicates an increase
**No pain reduction information available for the subset of the Reference group who never participated; 26% pain reduction for the subset who participated but did not move beyond level 1 - that subset completed all average of 3.4 performances of the first level exercise routine

TABLE 3

Odds ratios between groups for pre and post time frame*

| Outcome | Pre (OR [95% CI]) | Post (OR [95% CI]) |
|---|---|---|
| Total medical | 1.48 [0.57-3.86] | 0.91 [0.53-1.55] |
| Advanced imaging | 1.04 [0.53-2.06] | 0.27 [0.03-2.06] |
| Injection | 1.07 [0.52-2.21] | 0.53 [0.16-1.79] |
| ED/Urgent care | 0.53 [0.16-1.79] | 0 |
| Most frequent services | 1.50 [0.62-3.60] | 0.95 [0.55-1.62] |
| Opioid | 0.49 [0.27-0.88] | 0.15 [0.03-0.64] |
| Non-opioid | 0.57 [0.33-0.99] | 0.40 [0.20-0.80] |

*Ratios calculated with Participant group in numerator, i.e. values < 1 show lower odds in the Participant group The results demonstrate statistically significant reductions in total medical claims and number of individuals with prescriptions in the participating group of members. This embodiment of the present invention is associated with statistically significant and clinically meaningful improvements in medical claims, opioid and non-opioid prescriptions, and other clinical factors such as pain reduction. There is also evidence of potential reductions in consumption of specific services such as advanced imaging procedures and emergency or urgent care visits.

BRIEF DESCRIPTION OF THE DRAWINGS

Embodiments of the system and process are disclosed with reference to the accompanying drawings and are for illustrative purposes only. The system and process are not limited in their application to the details of construction or the arrangement of the components illustrated in the drawings. The system and process of use are capable of other embodiments or of being practiced or carried out in other various ways. In the drawings:

FIG. 3 is a mockup of an exemplary registration application page accessed through a browser by a member.

FIG. 4 is a mockup of an exemplary dashboard application page accessed with a browser by an administrator to provide manual member validation.

FIG. 6 is a mockup of an exemplary screening application page for screening, accessed by a member through a browser.

FIG. 7 is a mockup of another exemplary screening application page for screening, accessed by a member through a browser.

FIG. 16 is a mockup of an exemplary webpage within the dashboard application enabling an administrator to take action on a member's alert status using a browser.

FIG. 18 is a mockup of an exemplary webpage provided by the dashboard application and utilized by an administrator to review the list of members referred to a medical provider.

FIG. 19 is a mockup of an exemplary webpage provided by the dashboard application and utilized by an administrator to review the list of members in an alert status and the disposition of each alert.

FIG. 20 is a mockup of an exemplary member details webpage provided by the dashboard application and utilized by an administrator to review and update information about a specific member or manually intervene in a member's participation in the health engagement program.

DETAILED DESCRIPTION

Described herein is a system and process for managing members within health engagement programs. In at least some embodiments, the system and process are multi-phased and includes automated registration, validation, screening, triage, and care delivery for members in a health engagement program, using web-based interfaces, a mobile application, computer-based analyses, and web services to utilize data remotely gathered from the members and collected during use of a care delivery application containing assigned exercise routines and educational content. While the exemplary embodiments described herein reference a specific type of member, namely a member suffering from low back pain (LBP), it will be apparent to those skilled in the art that the invention may be used to screen, triage, and efficiently deliver care to members experiencing conditions other than LBP. As such, in at least some embodiments, the term "member" shall be understood to include an individual seeking to participate in a health engagement program, such as preventative care for a potential medical condition or management of a chronic medical condition (e.g., LBP, arthritis, etc.). In at least some embodiments, a member can be an employee, participant in a healthcare or wellness program, patient of a provider, or person covered under a qualifying insurance plan.

Exemplary embodiments of the system and process can include a plurality of user communication devices communicating with an application program via interactive portals and various web services and databases. The user communication devices can include various types of devices used to interface with other devices over wired or wireless communication networks, for example, mobile phones, tablets, laptops, workstations, etc. Exemplary web services can include, among others, a registration web service for processing members, a licensing web service controlling access to and rights within the system, and product web services for processing information entered by and collected about each member and corresponding activity within the system. In at least some embodiments, such web services may include gathering and analyzing screening activity to triage members into appropriate risk and care delivery categories. Various other types of web services can be utilized as well. Exemplary interactive portals can include web dashboards and browser interfaces to enter information, take action, and view member progression.

Figure 1:
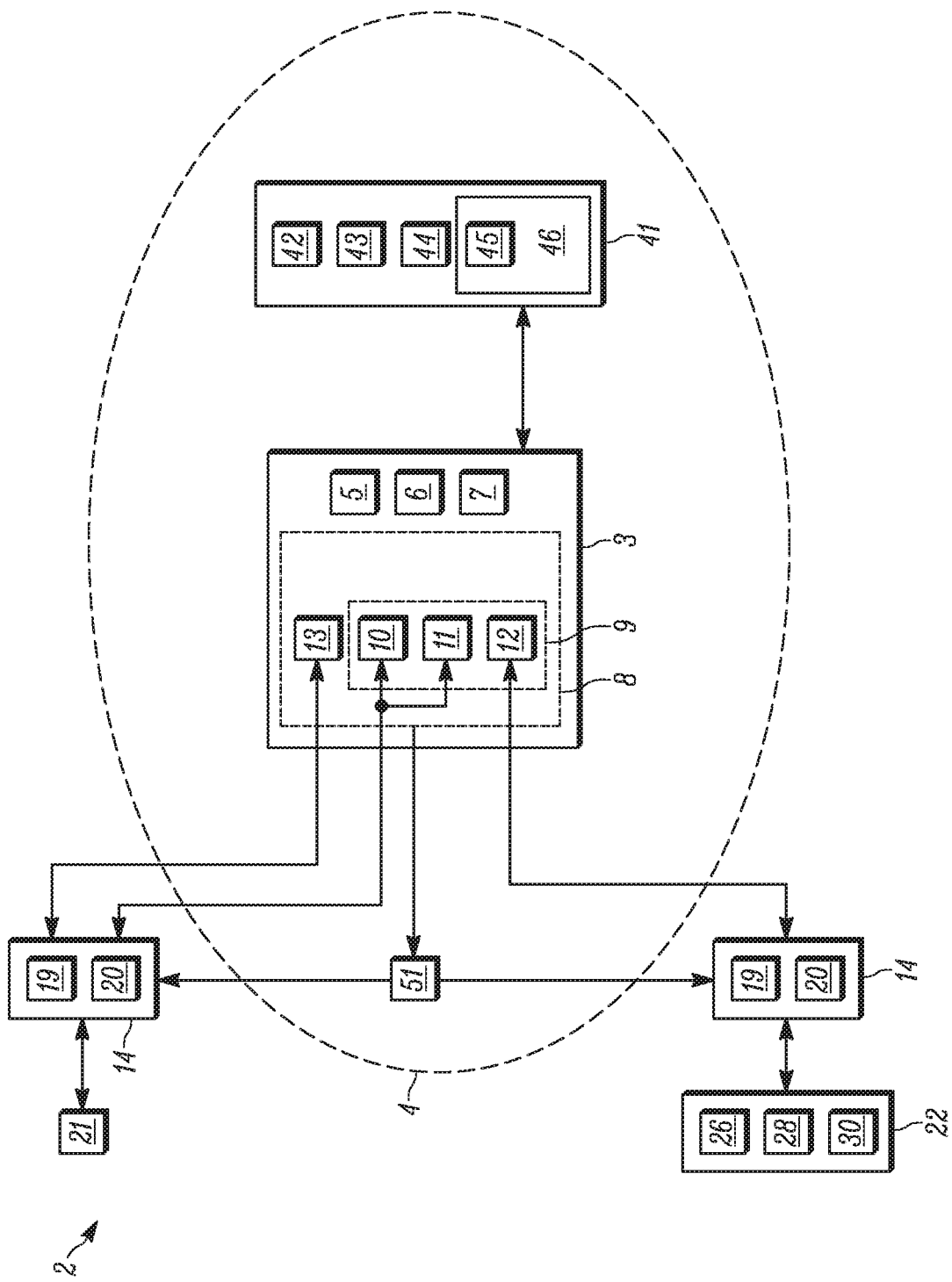
FIG. 1 is an exemplary block diagram representation of the system for performing the process for managing participation and progress in a health engagement program.
Figure 2:
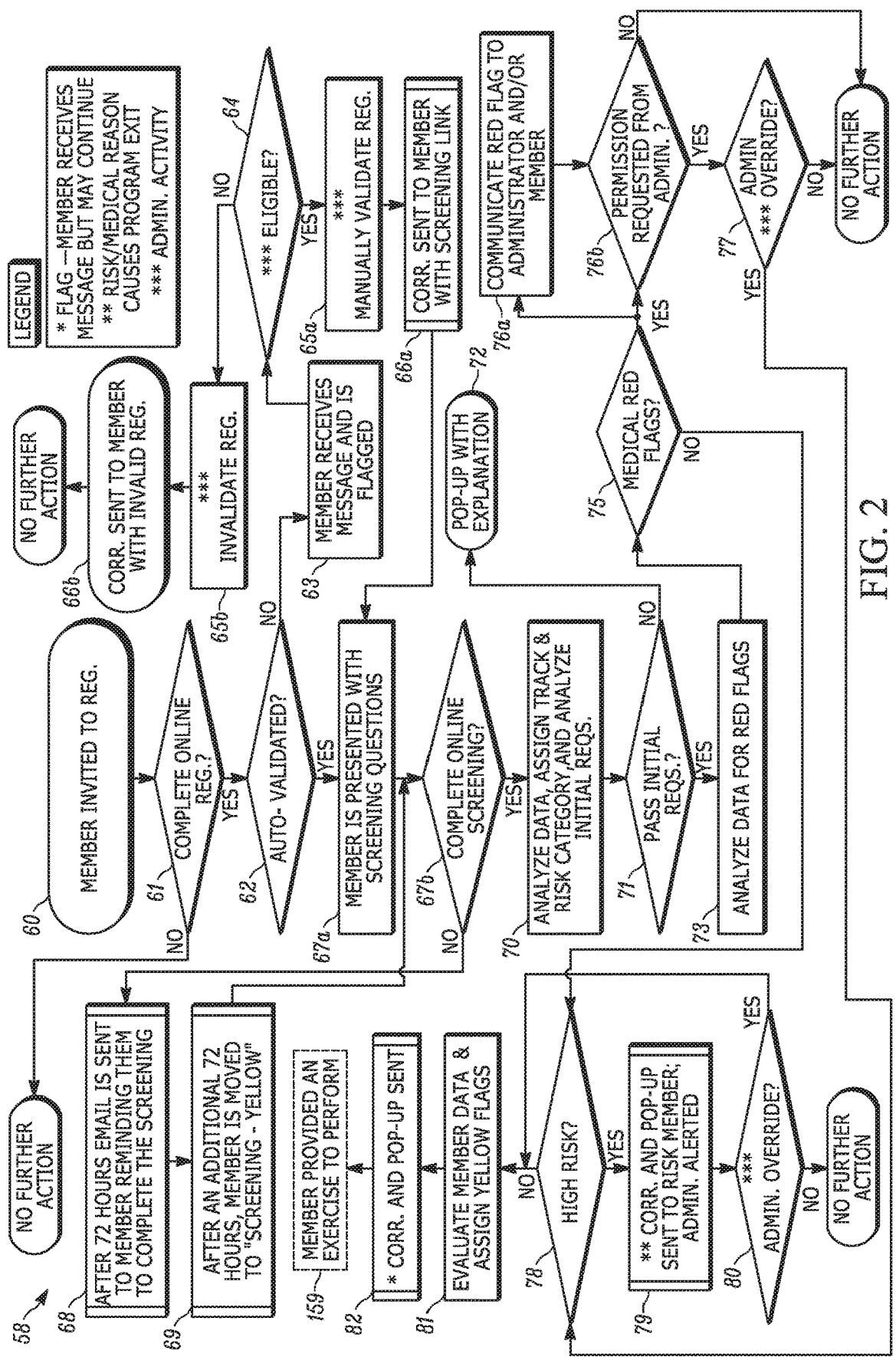
FIG. 2 is a flowchart of an exemplary first phase of the process for managing participation and progression in health engagement programs, directed to automated registration, screening, and triage.
Figure 5:
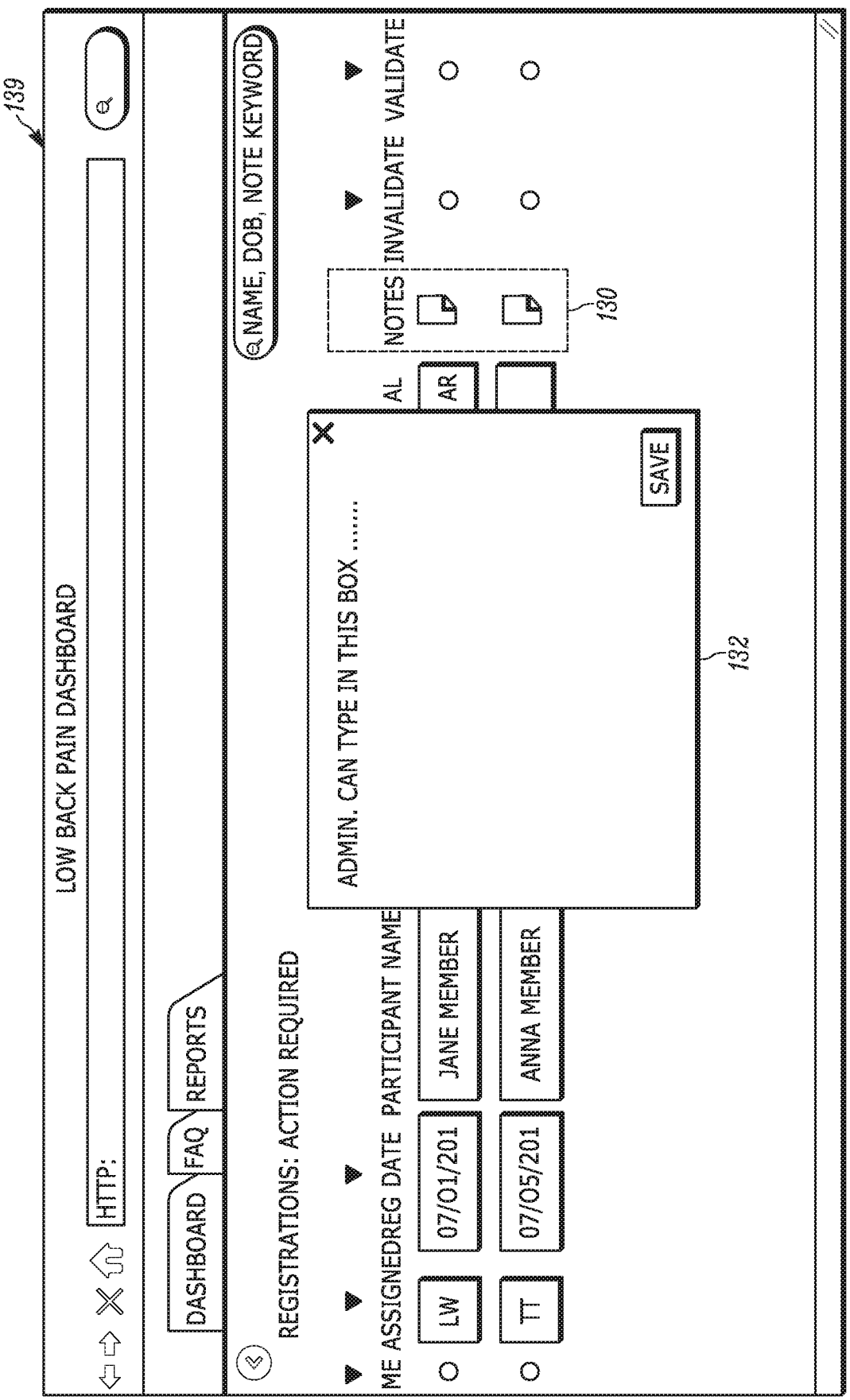
FIG. 5 is a mockup of an exemplary dashboard application page providing a notes page for the administrator.

Referring to FIG. 1, in at least some embodiments, the exemplary system 2 that facilitates the process for managing members within health engagement programs includes one or more servers 3, which can be on-premises or hosted in a cloud-based environment 4. The servers 3 can include one or more processors 5 (CPU), operating systems 6, memory and storage devices 7 (ROM, RAM, HDD, SSD, etc.), and one or more application programs 8 for executing the process described herein. The application program 8 is a computer program that can be accessed through several methods, such as one or more interactive web portals 9 communicating via local and/or remote networks (wired or wireless) (WAN, LAN, Cellular, Satellite, etc.), clients connecting through RESTful APIs, and via various types of web browsers. In other embodiments, the process and system can exist in any one of numerous other environments known in the art for interfacing hardware and software.

In one exemplary embodiment, the application program 8 comprises various web services, including a web-based registration application 10, a web-based screening application 11, a web-based dashboard application 12, and a care delivery application 13, each of which can be combined or segregated. Although various applications are identified as web-based, in at least some embodiments, they can be non-web-based. The application program 8 is network accessible through a plurality of communication devices 14, such as workstations (e.g., portable or stationary personal computers) and mobile devices (e.g., networked mobile phones, tablets, etc.), using a web browser 19 (i.e., web interface) or a mobile application 20. The web browser 19 or mobile application 20 can be used to provide a specific desired user interface tailored to the operating system and capabilities of the communication device 14, wherein the mobile application 20 can communicate directly with the application program 8. Although various processes are described herein as being performed in whole or in part by one of the mobile application 20 or the application program 8, it shall be understood that in at least some embodiments, one or more steps of the processes described herein can be performed by either the mobile application 20 or the application program 8, and therefore any description herein of the performance of a specific portion of any process shall not be interpreted as requiring exclusive performance via the mobile application 20 or the application program 8.

In at least some embodiments, as noted above, one or more portals 9 are used to facilitate communication between members 21 and administrators 22, and the application program 8. More particularly, the registration application 10 and screening application 11 can be accessed by the members 21 using a web browser (or mobile application), while the dashboard application 12 is accessed by the administrators 22 to monitor member progress, receive alerts, manually intervene with member progression (if deemed necessary), and interact with the members 21 and the application program 8. The application program 8 is in communication with one or more databases 41, which are accessible to obtain and store data. For example, a program database 42 can be provided to store data utilized by the program application 8 to perform various analyses as discussed below. Also, a dedicated database (e.g., administrator database 43) for a specific administrator 22 (e.g., company X), can be provided that includes data related only to company X's employees (members), while a company Y may be associated with another dedicated database for their employees. On the other hand, a shared-tenancy database 44 can be provided to store data provided by members 21 and administrators 22 from various organizations simultaneously. These databases 41 can be integral with or otherwise accessible by the server 3. In addition, various types of program related content 45 can be stored in a content database 46, as discussed further below.

It is to be understood that the communication devices 14 utilized by the members 21 and administrators 22 can include various types of well-known hardware and operating systems (e.g., IOS, ANDROID, LINUX, WINDOWS, etc.) that allow for communication with other devices, using wired or wireless methods, display graphical information, provide audio outputs, receive audio and camera-based inputs, etc. Examples of such communication devices 14 can include an "IPHONE X," as manufactured by Apple Inc., a "GALAXY NOTE 9", as manufactured by Samsung, etc.

Various types of individuals and organizations can be operatively functional in the system 2. For example, in at least some embodiments, such as shown in FIG. 1, the administrator 22 can include one or more of various types of individuals/entities. Some examples of an administrator 22 can include, a program administrator organization ("care manager") 26, an insurance company ("payer") 28, personnel at a medical provider ("provider") 30, etc. The members 21 can include one or more of various types of individuals that wish to utilize the system 2 to enhance their health, such as an employee, a participant in a healthcare or wellness program, a person covered under an insurance plan, etc. It shall be understood that in at least some embodiments, the term administrator 22 is intended to comprise any one or more of various types of personnel that can serve an administrative function to assist with the process disclosed herein.

The process for managing participation and progression in health engagement programs can include multiple phases. In at least some embodiments, the process includes two phases, a first phase that includes automated registration, screening, and triage, and a second phase that includes automated care delivery and progression. Referring to FIGS. 1-7, an exemplary flowchart 58 of the first phase of the process is provided in FIG. 2, which includes automated registration, screening, and triage (e.g., track and risk analysis). The first phase begins at step 60, with the member 21 being invited to participate in the program by an administrator 22, which can occur for example, via a correspondence, such as an email message, direct notification through an Electronic Health Records (EHR) system, or an open invitation on a website or through other channels. In at least some embodiments, the member 21 utilizes the communication device 14 to communicate with the registration application 10, such as through the portal 9, and completes the registration process by providing the required information (e.g., demographic and eligibility information). The registration process utilizes the registration application 10 to communicate a plurality of registration-based queries to the member 21, and to receive a plurality of registration-based query responses from the member 21 in response. The registration-based queries can include numerous types of questions, as discussed further below.

Figure 3:
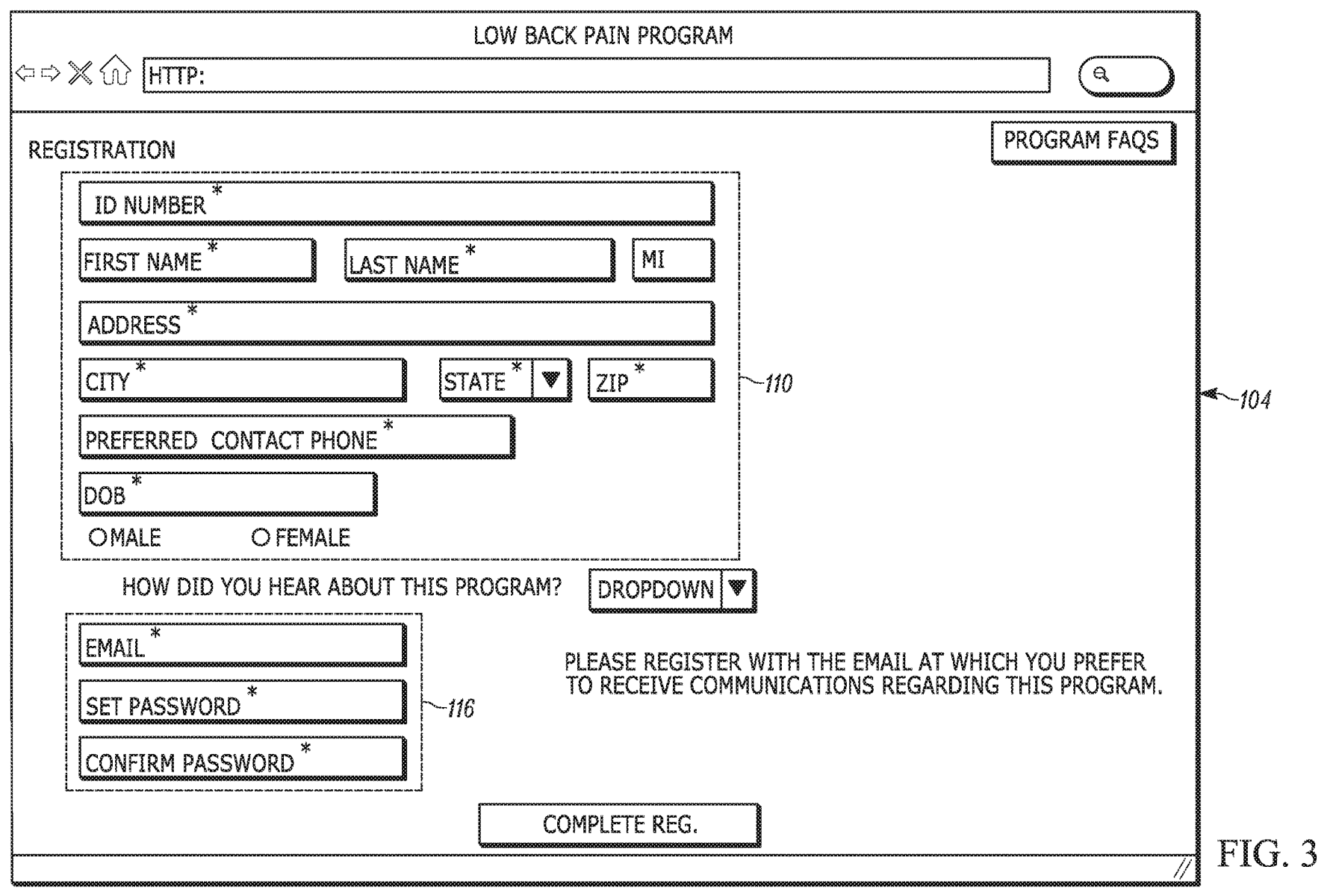

FIG. 3 contains a mockup of an exemplary web page 104 presented by the registration application 10 during registration and showing exemplary registration-based queries, which can include exemplary member identification data 110, such as an ID Number, name, address, contact details, demographic information, gender, etc. The web page 104 also requests the member 21 to establish login credentials 116, such as an email address and password, which are utilized for later for authentication. Information provided by the member 21 is stored in one of the databases 41, such as the administrator database 44.

Once the member 21 has completed the registration-based queries presented by the registration application 10 in step 61, then at step 62, the member-specific information stored in one of the databases 41 is compared by the application program 8 against a known list of eligible individuals provided in the same or another database 41 (e.g., administrator database 44). If the member 21 is found in the list, then she/he is automatically validated in step 62. Members 21 who are automatically validated progress to screening in step 67a. If the member is not automatically validated in step 62, then the process advances to step 63, where the application program 8 communicates a message to the member 21 notifying them of validation failure. The notification can be sent using any one of various known means, which can include a pop-up window, or a command from the application program 8 to a notification service 51 (e.g. a commercial Push Notification or Email Service) that sends a notice to the member 21 for receipt by the communication device 14. In addition, at step 63, the failure to validate is flagged by the application program 8 and the administrator 22 is notified (e.g., via the dashboard application 12), at this point the failure to validate has been queued for review in step 64. In at least some embodiments, the dashboard application 12 is utilized by the administrator 22 to view the details related to the invalidation.

Figure 4:
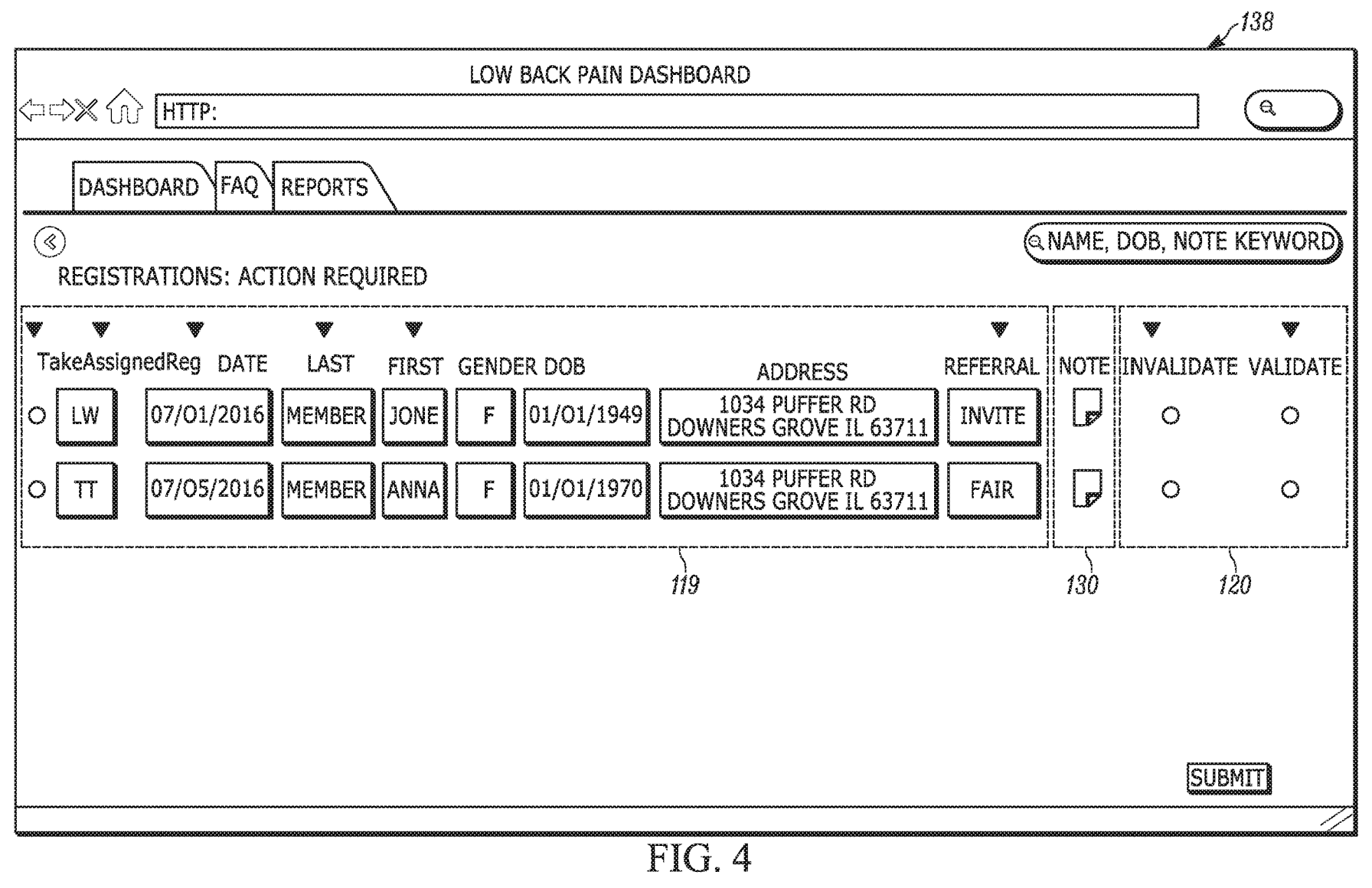

In step 64, the administrator 22 confirms the eligibility status of the member 21 and has an opportunity to manually validate using the dashboard application 12 for example (see FIG. 4). Individuals determined by the administrator 22 to be eligible to participate in the program during step 64 are then manually validated in step 65a, and receive correspondence that can include a screening link in step 66a, and the process proceeds to step 67a. The screening link can include any type of means to allow the member 21 to access the screening application, such as a hyperlink, button, token, etc. Members 21 determined to be ineligible at step 64 are marked invalid by the administrator 22 in step 65b and are then notified in step 66b that their registration is invalid, and they are excluded from participation.

FIG. 4 includes an exemplary dashboard webpage 138 provided by the dashboard application 12 via the portal 9. As shown, a manual validation selection 120 can be utilized by the administrator 22 to manually validate or invalidate any member 21 that failed the automated validation process 62, as discussed above in step 64. In at least some embodiments, the administrator 22 can select a notes option 130 for a member 21 and then enter notes in the resultant popup box 132, as shown in the exemplary webpage 139 in FIG. 5. Such notes can be stored in one of the databases 41 and accessible by the administrator 22 through one of the portals 9.

Members 21 that have been validated are provided an opportunity to complete online screening in step 67a, which includes interfacing with the screening application 11. Screening includes presenting screening-based queries to the member 21 from the screening application 11 and storing the selected screening-based query responses in one of the databases 41. The screening-based queries can include any of numerous questions selected to identify the member's state of health, availability of interfacing technology, health history, goals, etc. If the member 21 fails to complete the screening as queried in step 67b, then in step 68 after a specific time duration has expired (e.g., 72 hours), a reminder correspondence (e.g., email) is sent to the member 21, and if after yet another specific time duration has expired (e.g., 72 hours) without completion, then in step 69 the screening process is flagged (e.g., yellow flag) for that member 21 and the administrator 22 is notified to assist with encouraging the member 21 to complete screening.

Referring to FIGS. 6 and 7, exemplary screening webpages 140 and 142 are shown that are presented by the screening application 11 to the member 21. Webpage 140 illustrates exemplary screening-based queries, such as initial questions 144 about care history, access to technology, and preference for provider location, while screening webpage 142 includes various exemplary medical history and symptom questions 146. As should be understood to those skilled in the art, the screening-based queries can include a wide variety of inquires that can be general or very specific depending on the nature of the potential services and specific issue the member 21 is looking to manage. In at least some embodiments, the screening-based queries can be completed in whole or in part by the member 21, or by a medical provider 30 acting on behalf of the member 21, and all data and screening-based query responses are stored in one of the databases 41.

Continuing the process at step 70, the data gathered during the screening process is analyzed at step 70, and each member 21 is assigned a specific track and risk level based on various criteria. In at least some embodiments, the criteria can be predefined based on the types of condition reported by the member 21, guidelines provided by the administrator 22, or other criteria provided by a medical professional and that relates to a specific type of health management program. In at least some embodiments, the assignment of the track and risk levels can include utilizing the application program 8 to apply heuristics gathered from a plurality of experienced professionals who perform associated medical assessments and treatments. As noted, each member 21 can be assigned to an appropriate exercise track (e.g., A, B, or C) to address the individual's specific condition detailed during the screening process. The individual exercise tracks are designed to impact variations of a condition that surface under different scenarios (e.g. sitting vs. standing, etc.). Appropriate risk levels (High, Medium, Low, etc.) are also assigned to each member 21 based on gathered data.

Further in step 70, the data is also evaluated to check if the member 21 meets various initial requirements for program participation, such as having a supported communication device, etc. If the initial requirements for program participation are not met, as queried in step 71, then at step 72 an explanation message is provided to the member 21 informing them of the problem. If a member 21 meets the initial participation requirements at step 71, then the process moves to step 73 where the screening application 11 analyzes the member's data for any medical red flags. Red flags can include any of various conditions that indicate a member 21 should consult with their healthcare provider prior to participating in the program, such as shown in the exemplary Q/A in Table 4 below which provides sample questions and answers that could be provided during the screening process, and whether the screening application 11 would classify the answer as indicating a medical red flag.

occurs. In at least some embodiments, the notification and/or override process can be processed outside of the application program 8, communicating results as needed to the application program 8 or the mobile application 20.

In step 78, the member's risk category is checked to see if it was deemed High in step 70. If so, then the process moves to step 79 where member 21 is alerted (e.g., email, pop-up, etc.) and the risk issue is annunciated to the administrator 22 via the dashboard application 12. In step 80, the process monitors for an override command that can be provided by the administrator 22 via the dashboard application 12, to allow the member 21 to advance to step 81. If an override is not provided, no further action is taken.

If the member 21 was not identified as high risk in step 78, or if an override command has been executed in step 80, then the process moves to step 81 where the screening application 11 evaluates the member's data to identify any yellow flags (i.e. warnings) that should be attributed to the member 21 for future reference. Yellow flags are issues deemed relevant to monitor (e.g., a past diagnosis of cancer, or leg pain, numbness or tingling that is more bothersome than the principal issue identified by the member (e.g., back pain)), but not significant enough to prevent participation in the

TABLE 4

| | |
|---|---|
| Has your healthcare provider told you to avoid gentle exercise? | Yes = Medical Red Flag |
| (PRIMARY) Did your current low back pain begin after a recent injury? | |
| IF YES → Have you been seen by a healthcare provider for this injury? | No = Medical Red Flag |
| (PRIMARY) Do you have trouble starting or stopping the flow of urine or feces? | |
| IF YES TO PRIMARY (Secondary 1) Has this trouble started in the past 2 weeks? | Yes = Medical Red Flag |
| IF NO TO SECONDARY 1 (Secondary 2) Has this trouble gotten slowly worse over time? | Yes = Medical Red Flag |
| Do you have numbness in the area of your bottom where you would sit on a bicycle seat? | Yes = Medical Red Flag |

In at least some embodiments, if a medical red flag is indicated at step 73, the member 21 and/or administrator 22 are notified of the red flag at step 76a, and the process advances to step 76b, where the application program 8 checks if the member 21 has requested an override from the administrator 22, such override permission to be based, for example, on the member obtaining clearance from appropriate medical personnel. If permission is sought, the screening application 11 can send a notification to the administrator 22 requesting the override. The administrator 22 can override the medical red flag at step 77 through the dashboard application 12 to thereby allow the member 21 to continue in the program, advancing the process to step 78. If an override is not granted at step 77, then no further action process. Upon completion of step 81, notification is provided in step 82 to the member 21 (e.g., email, pop-up window) and administrator 22 (e.g., via the dashboard application 12), and the member 21 advances to phase 2 of the process (step 159 FIG. 8) to begin the program.

Although the application program 8 can be utilized to implement various types of health engagement programs and should not be construed to be limited to any particular type of health engagement programs, in an exemplary embodiment described herein, the application program 8 is utilized to implement a low back pain (LBP) health engagement program, with one example of the registration and screening process summarized below in Table 5.

TABLE 5

| | | Resulting Classification | | |
|---|---|---|---|---|
| Screening Level | Screening Type | Qualified Candidate for Digital Care Pathway | | Screened Out |
| Pre- | Registration | Validated for LBP Program | | Not Eligible |
| 1 | General Eligibility | Eligible and equipped for LBP Program | | Not Eligible |
| 2 | Medical Appropriateness | No Medical Flags | Medical Yellow Flag | Medical Red Flag |
| 3 | Psychological Appropriateness | Low Risk | Medium Risk | High Risk |
| 3 | Pain & ADL Baselines | Baseline Values Stored | | Baseline Values Stored in database |

TABLE 5-continued

| Screening Level | Screening Type | Resulting Classification | | | |
|---|---|---|---|---|---|
| | | Qualified Candidate for Digital Care Pathway | | | Screened Out |
| 4 | Symptom Specific | Exercise Track A | Exercise Track B | Exercise Track C | Track Stored in database but content is not delivered |

The screening questions and analyses for determining the resulting classifications are in at least some embodiments, specifically tailored for each administrator 22 responsible for the member 21. As such, for a specific health engagement program, the administrator 22 can customize the screening questions presented by the screening application 11, as well as one or more of the analyses used when analyzing the answers to the screening questions. For example, in at least some embodiments, the appropriate exercise track can be determined by the nature of the activity which surfaces/aggravates the condition, as gathered during the screening process. More particularly, members 21 whose condition is surfaced/aggravated by sitting and driving can be classified into Track A (Extension track), members whose condition is surfaced/aggravated by standing and walking can be classified into Track B (Flexion track), and members whose condition is surfaced/aggravated by both sitting and standing can be classified into Track C (Non-directional track). These exemplary track classifications may be appropriate for an LBP health engagement program, but not for another health engagement program that may, for example, be focused on knee, neck, cardiovascular health, or any number of other conditions. As such, other health engagement programs can include different classifications. In at least some embodiments, the extension track includes exercises specifically designed to improve spinal extension, such as prone on elbows, while the flexion track includes exercises specifically designed to improve spinal flexion, such as double knees to chest, and the non-directional track includes both exercises specifically designed to improve both spinal flexion and exercises specifically designed to improve spinal extension, such as bridging and single knee to chest.

Similarly, risk level assignment can be determined according to the specific type of health engagement program and/or the administrator 22. In at least some embodiments, assessment can conform to standards that are well known in a field related to the particular program. For example, there are several widely used and accepted classification systems used to guide the prescription of therapeutic exercise for LBP. One such classification system is the Treatment Based Classification (TBC) system. This classification system can be used to establish decision-making criteria to assist in better triaging patients to medical management, rehabilitation management or self-care management. The TBC system advises that sufferers of LBP can be broken into three groups by utilizing psychosocial risk stratification tools to determine: 1) which high risk patients require medical attention; 2) which low risk patients are appropriate for self-care; and 3) which medium risk patients can participate in exercise, but may still require concurrent referral to medical professionals.

One such stratification tool is the Subgroups for Targeted Treatment ("STarT") Back Screening Tool. "STarT" was specifically developed and validated to provide a simple, brief, and practical way to subgroup patients with nonspecific LBP. In at least some embodiments, the tool includes nine item questions pertaining to: referred leg pain, comorbid pain, disability (2 items), bothersomeness, catastrophizing, fear, anxiety, and depression. The latter 5 item questions are identified as a psychosocial subscale. Patients scoring 4 or 5 on a psychosocial subscale are classified as high risk. Those scoring 0-3 on the primary scale are classified as low risk. Those scoring higher than 3 on the primary scale, but less than 4 on the subscale are classified as medium risk. The "STarT" Back Screening Tool is available from KEELE University, Staffordshire, UK, and although it can be used in at least some embodiments to assign risk level for health engagement programs specific to LBP, other known classification systems can also be utilized, including less formalized classification systems utilized by health professionals and related health engagement programs.

Figure 8:
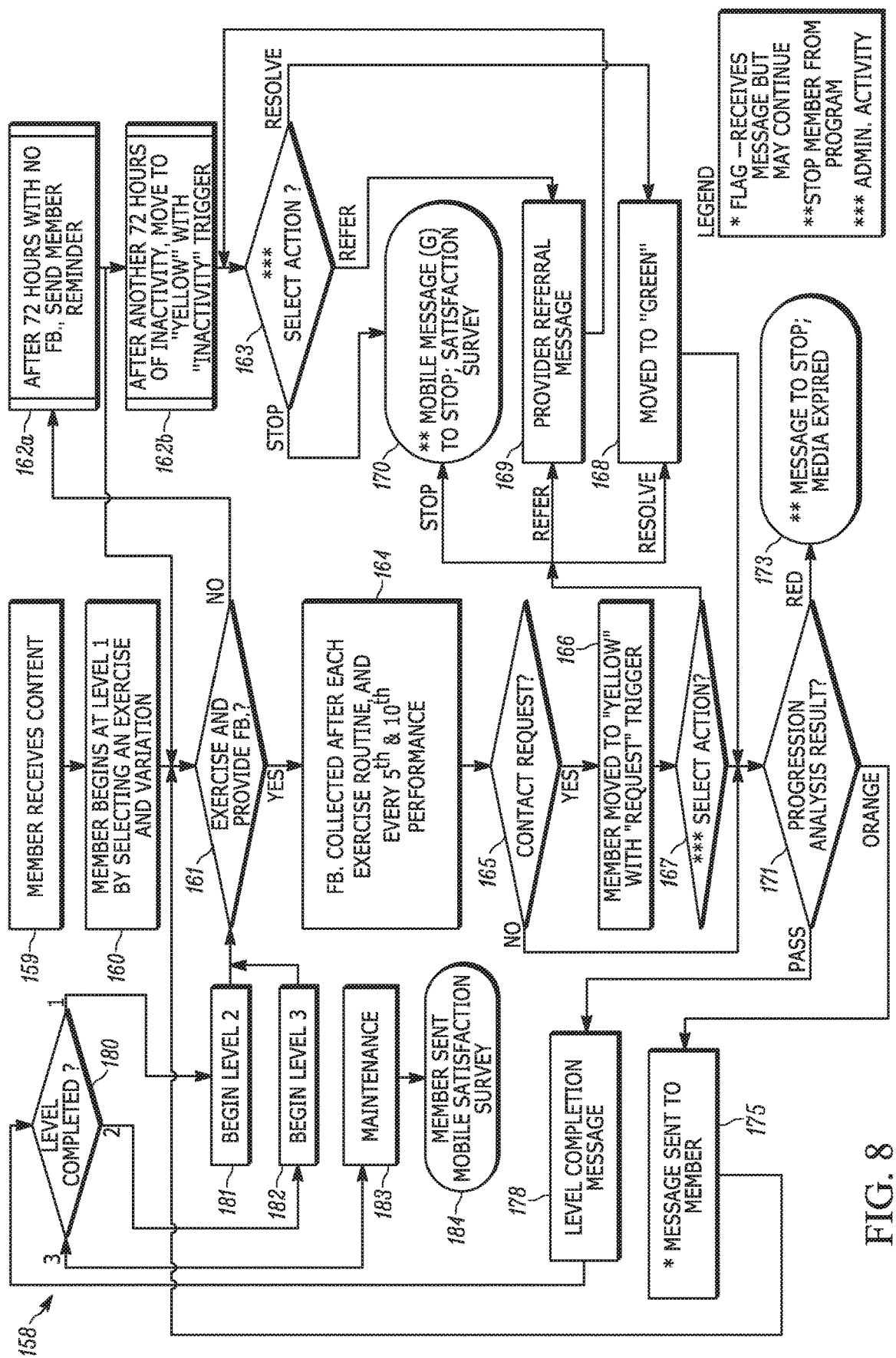
FIG. 8 is a flowchart of an exemplary second phase of the process for managing participation and progression in health engagement programs, directed to automated care delivery and progression.

As discussed above, phase 1 of the process is centered around registering and screening a member 21 for participation in a particular health engagement program that involves interaction with the care delivery application 13 and content 45. Upon successful completion of phase 1 (i.e., the member not screened out), such as illustrated in flowchart 58, the member 21 advances to phase 2 of the health engagement program in the track that was assigned to them in step 70. FIG. 8 provides a flowchart 158 that details the progression of an exemplary care delivery program that involves the member interacting with the care delivery application 13.

The member 21 utilizes the mobile application 20 or other communication device 14 to interface with the program application 8, which provides a plurality of levels for member progression. As shown in the flowchart 158, the member 21 begins at step 159, in level 1 of their assigned track with the care delivery application 13 communicating corresponding content 45, which potentially includes an exercise routine (i.e. collection of assigned exercises) to the member 21. This is a tailored routine that can include various exercises, reps, and sets, along with other content, designed and aligned to improve each member's specific condition and symptoms based on the track selected in the screening process. The specific exercises, reps, and sets provided to the member 21 can vary as desired or directed based on the type of program (e.g., LBP). It is to be understood that in at least some embodiments, the content provided to the member 21 is selected from a plethora of exercises known to persons skilled in the art (e.g., physical therapists, medical doctors, etc.) for treatment of a particular issue (e.g., straight leg raises for knee pain, double knees to chest for low back pain aggravated by standing, and press ups for low back pain aggravated by sitting, etc.). In at least some embodiments, the exercise routine accessible to the member 21 includes an animation depicting a representative human rendering performing the exercise routine, while in other embodiments, the exercise routine can take the form of a video or still images of an actual human performing the exercises.

Figure 9:
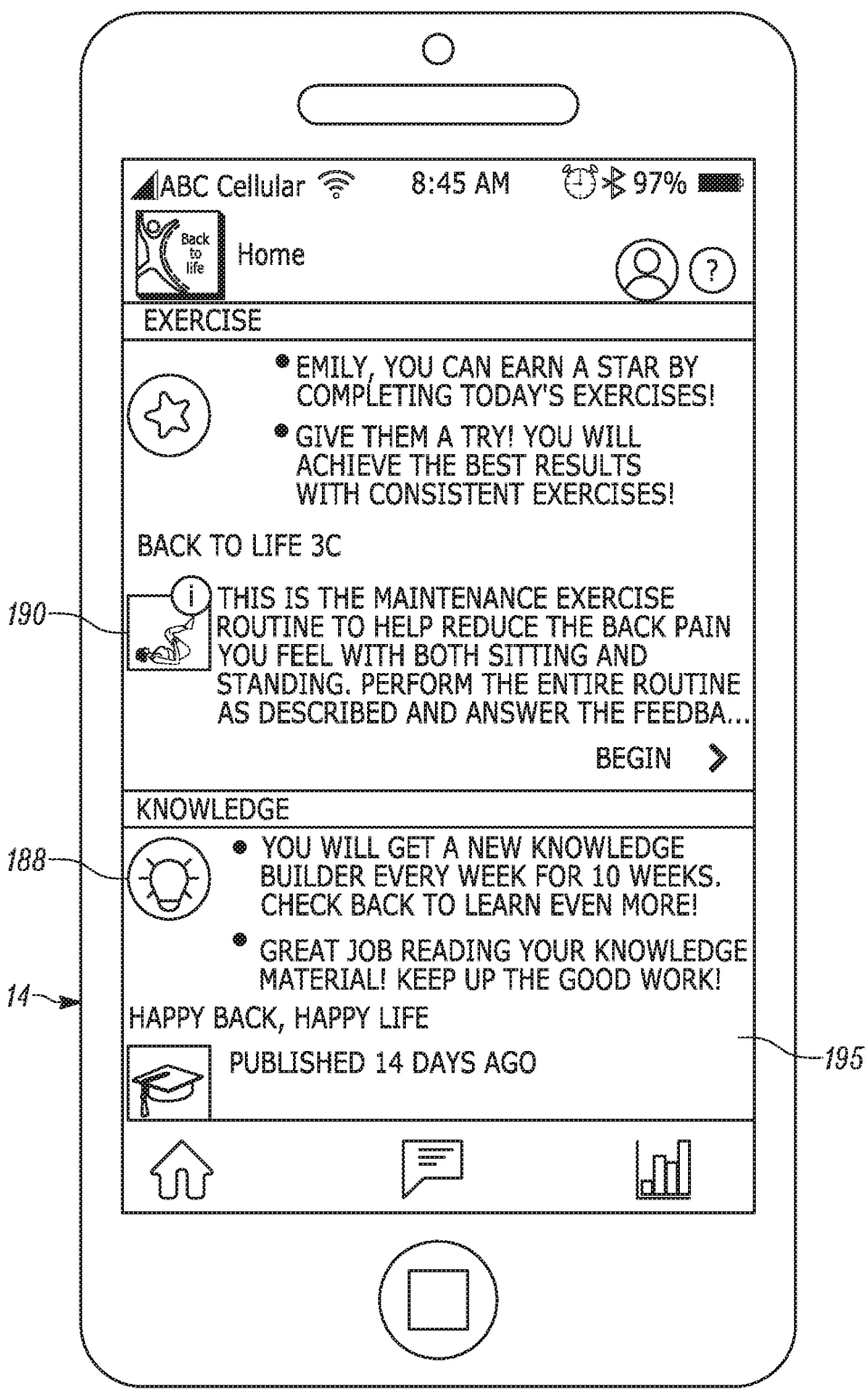
FIG. 9 is a mockup of a screen provided by an exemplary mobile application running on an exemplary communication device, offering an exemplary selection of content to a member.
Figure 10:
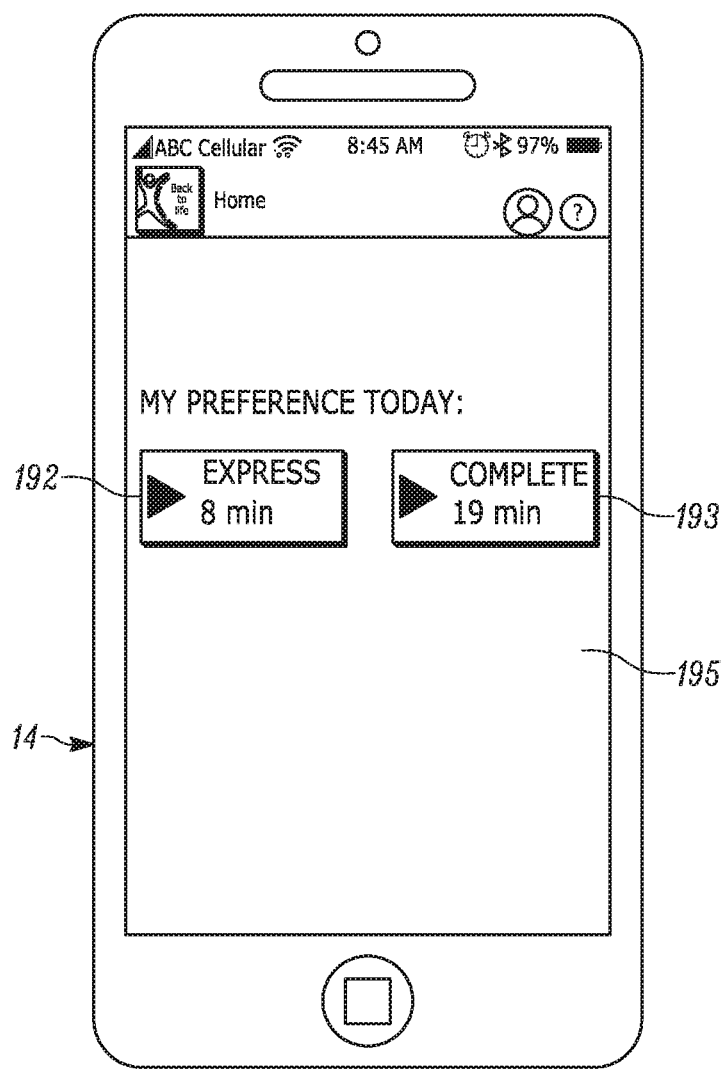
FIG. 10 is a mockup of a screen provided by the mobile application offering an exemplary selection for a desired variation of the assigned exercise routine.
Figure 11:
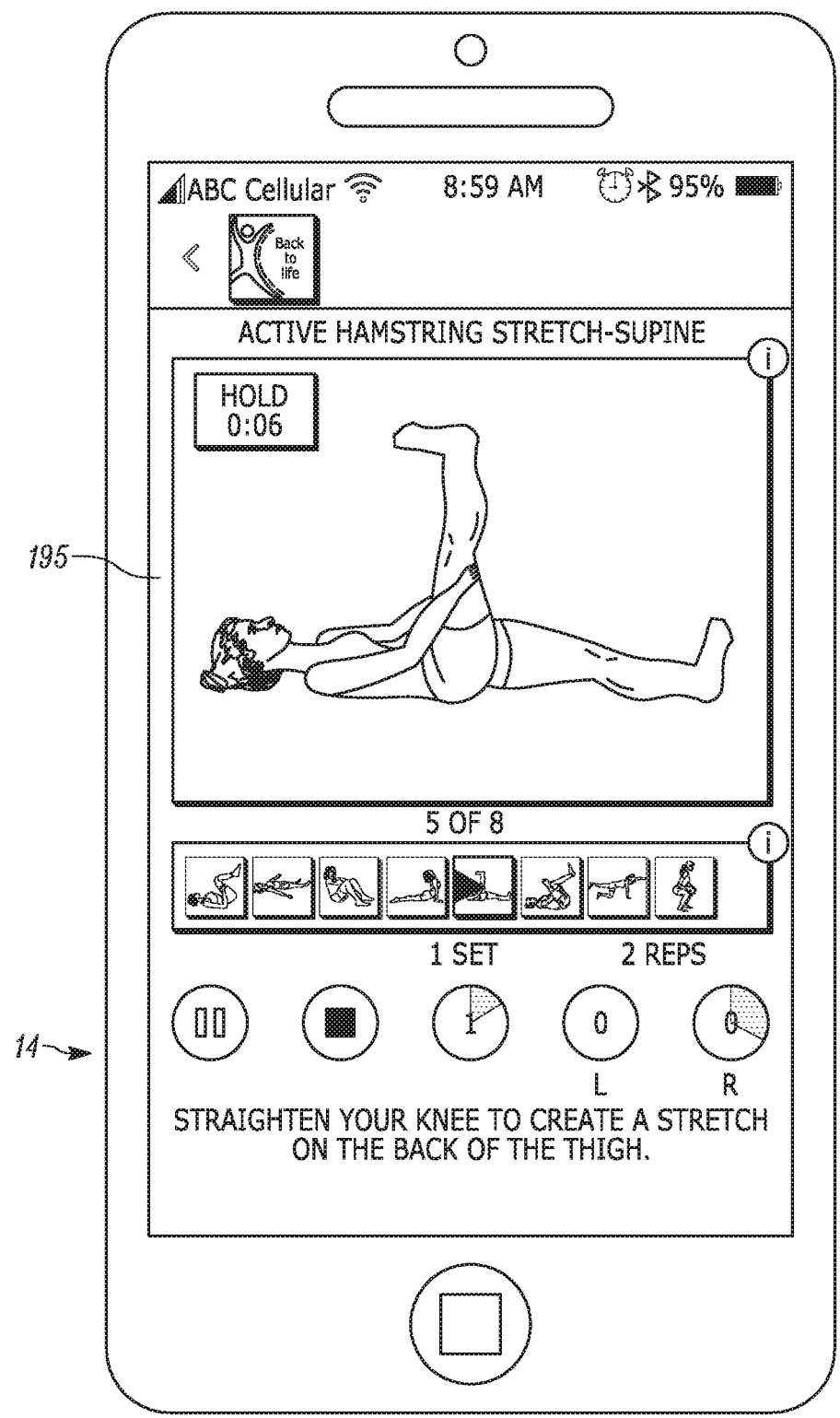
FIG. 11 is a mockup of exemplary content provided for an assigned exercise routine.
Figure 12:
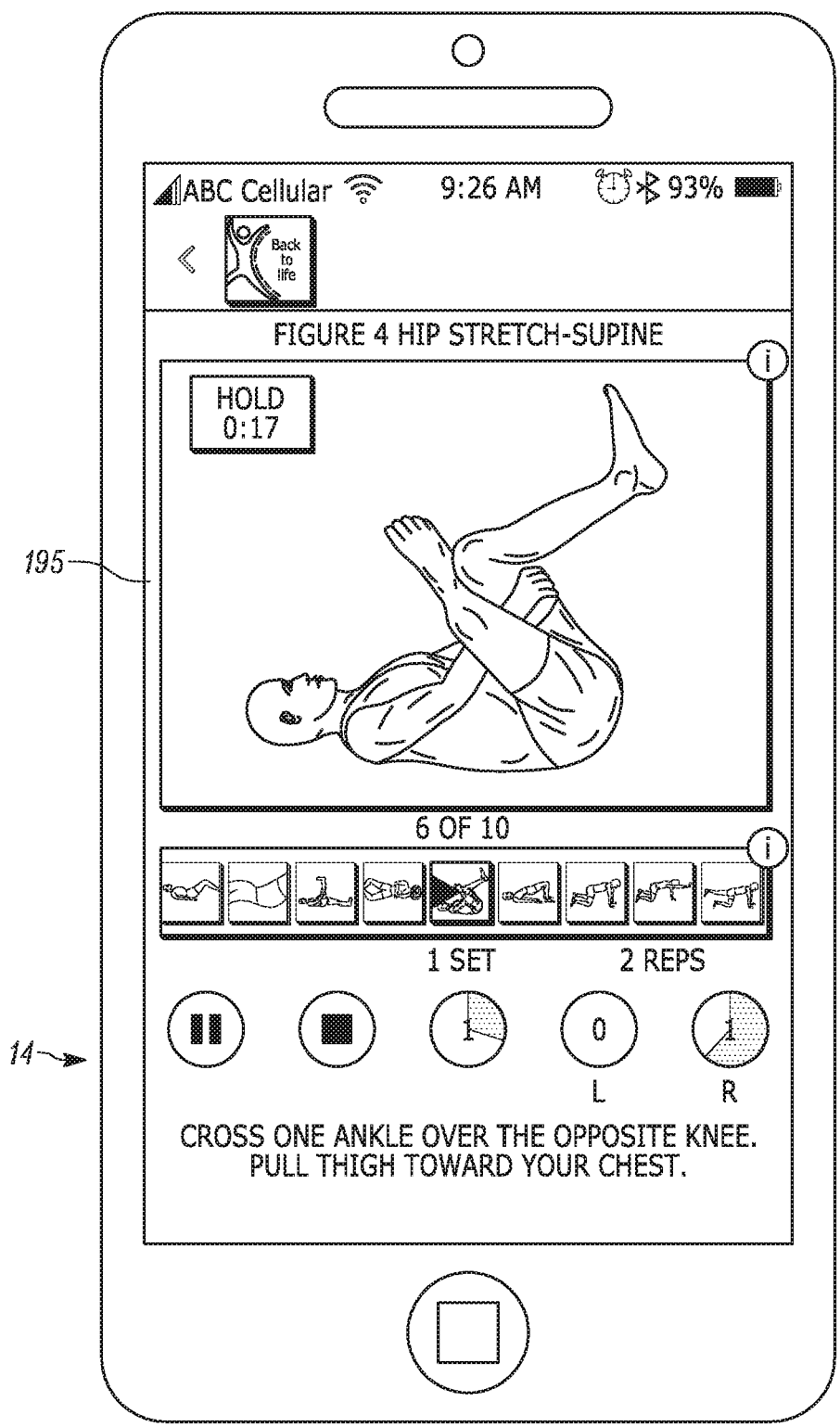
FIG. 12 is another mockup of the displayed exemplary content for an assigned exercise routine.

The member 21 is presented content 45 that is to be provided by the care delivery application 13 and displayed via the mobile application 20, wherein in addition to exercise routines, the content 45 can further include educational materials (e.g., knowledge articles) for the member 21 to view. FIG. 9 includes a mockup of the mobile application 20 on the member's communication device 14, demonstrating the capability for the member 21 to select exemplary educational materials 188 to view or assigned exercises 190 to perform. In at least some embodiments, the member 21 can be offered the option to choose between variations of the assigned exercise routines and educational materials. FIG. 10 includes a mockup of the mobile application 20 offering an option to select between exemplary variations (versions) of the assigned exercise routine 190, such as an abbreviated variant ("Express") 192 and non-abbreviated variant ("Complete") 193. This option enables the member 21 to choose the most appropriate version for each performance based on their condition and/or the amount of time available to complete the routine. The resulting selection enables playback, on a display 195 of the member's communication device 14, of the routine reflecting the appropriate exercises, repetitions, sets, and duration as provided by the care delivery application 13. Upon completion of the routine, the selected routine and variation are recorded in one of the databases 41. In at least some embodiments, the assigned exercises 190 presented to each member 21 can include animations and content tailored to the preferred gender, as well as information provided by the member 21. FIG. 11 and FIG. 12 include mockups of exemplary assigned exercises 190 as presented in the mobile application 20, such as an Active Hamstring Stretch (FIG. 11) and a Hip Stretch (FIG. 12), where it can be seen that the member 21 is further presented with playback control option buttons (e.g., pause, stop, etc.) and exercise sequence selections, so the member 21 can execute program control during performance.

Figure 13:
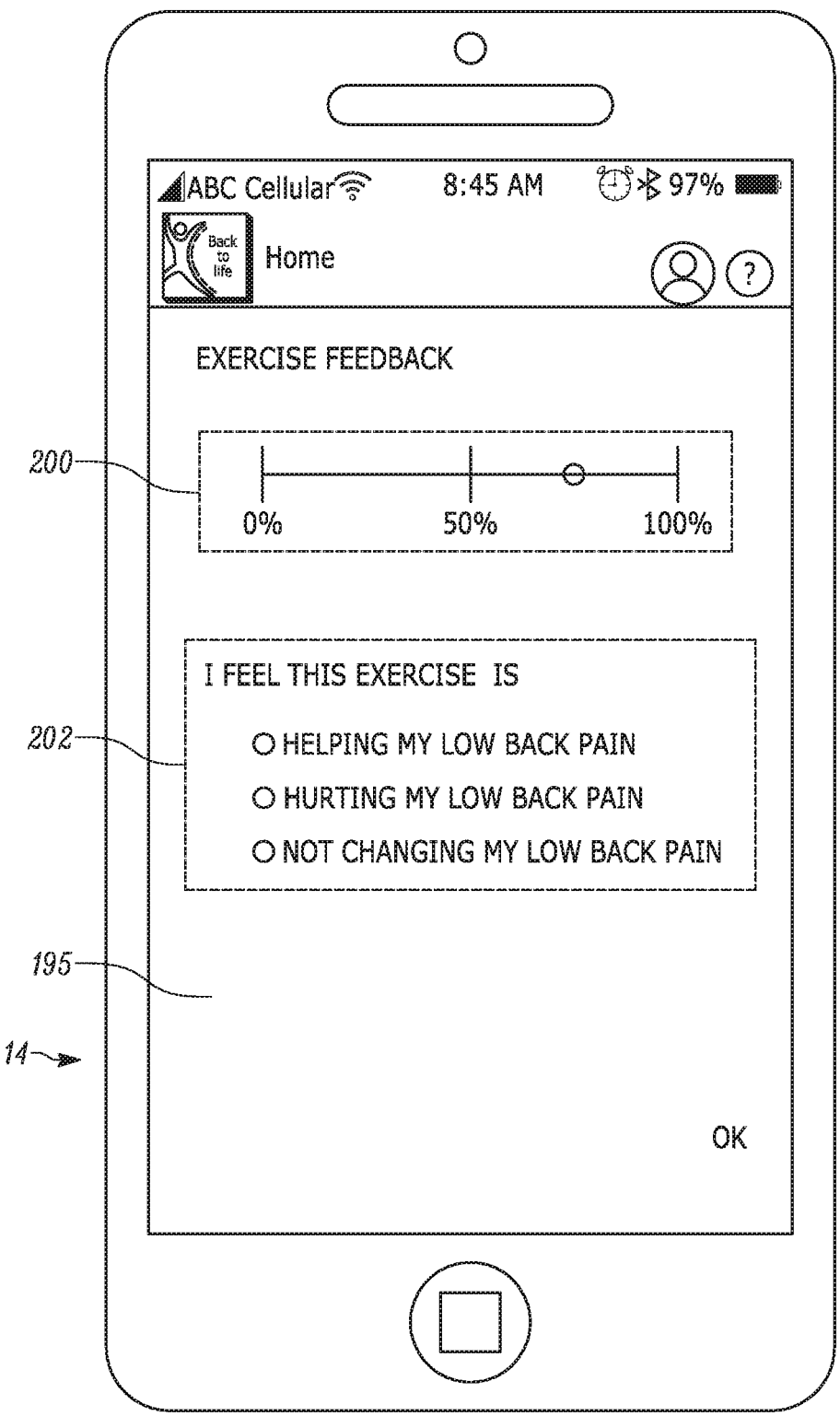
FIG. 13 is a mockup of an exemplary exercise survey that members complete at the end of each exercise.
Figure 14:
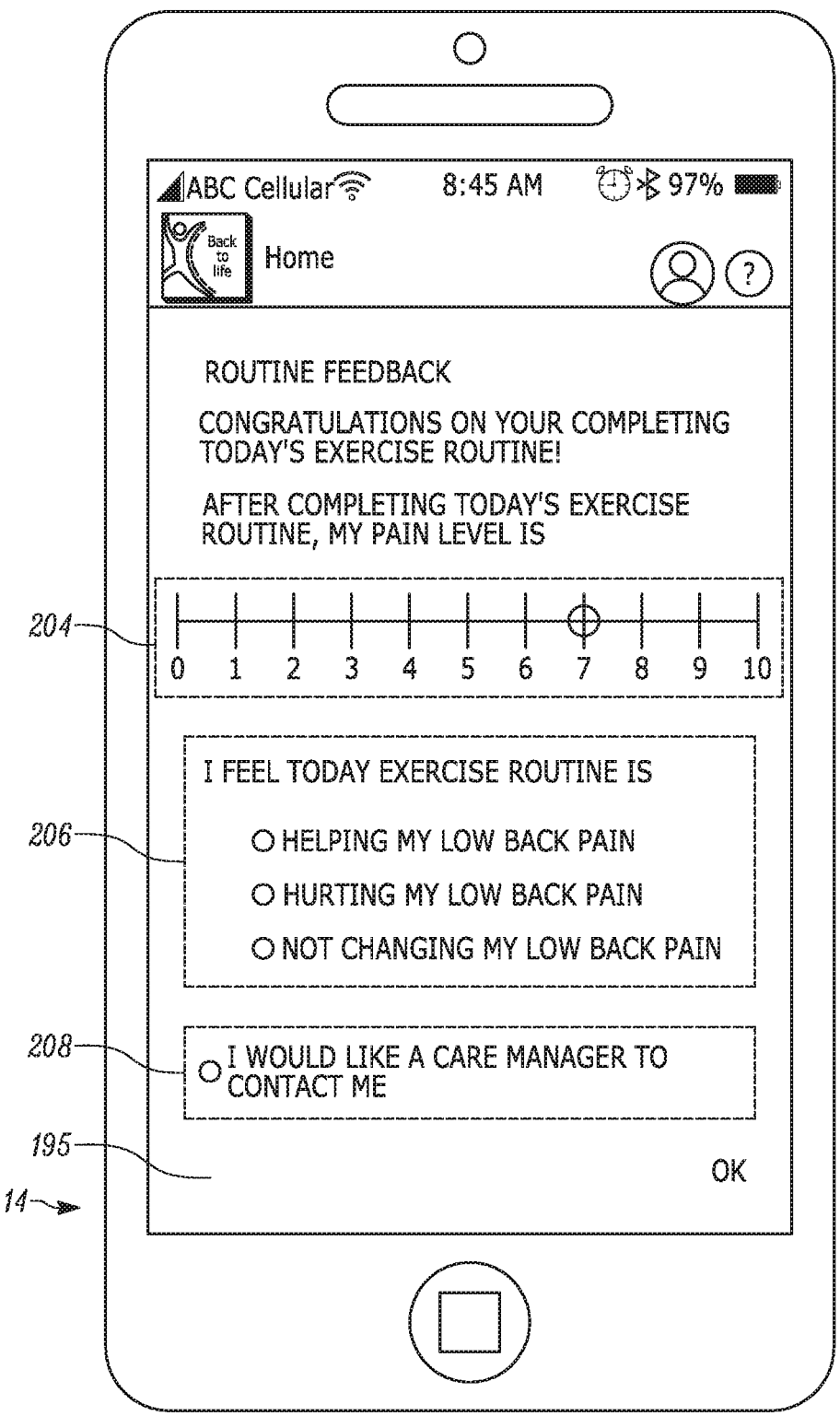
FIG. 14 is a mockup of an exemplary routine survey members complete at the end of each routine.

Referring back to FIG. 8, in step 161 after the member 21 performs the assigned exercises as directed via the mobile application 20, they are directed to provide feedback at step 164. The member 21 utilizes the mobile application 20 to complete assigned exercises and provide feedback after each performance through exercise, routine and program surveys, which gather perceptions on pain, functional ability, reported adherence (completion %), and how the exercise, routine, or program is impacting the condition. FIG. 13 provides a mockup of the screen, presented to a member 21 on the display 195, of an exemplary exercise feedback screen for gathering reported adherence 200 and the member's perception of the exercise's impact on the condition 202. After performing each routine, the member 21 is presented with a routine survey to provide additional feedback including the overall impact on the condition. FIG. 14 provides a mockup of an exemplary routine feedback survey that includes a pain level scale 204, an exemplary question 206 about the perceived routine's impact on the condition, and queries if the member 21 would like the administrator 22 to contact the individual 208.

Figure 15:
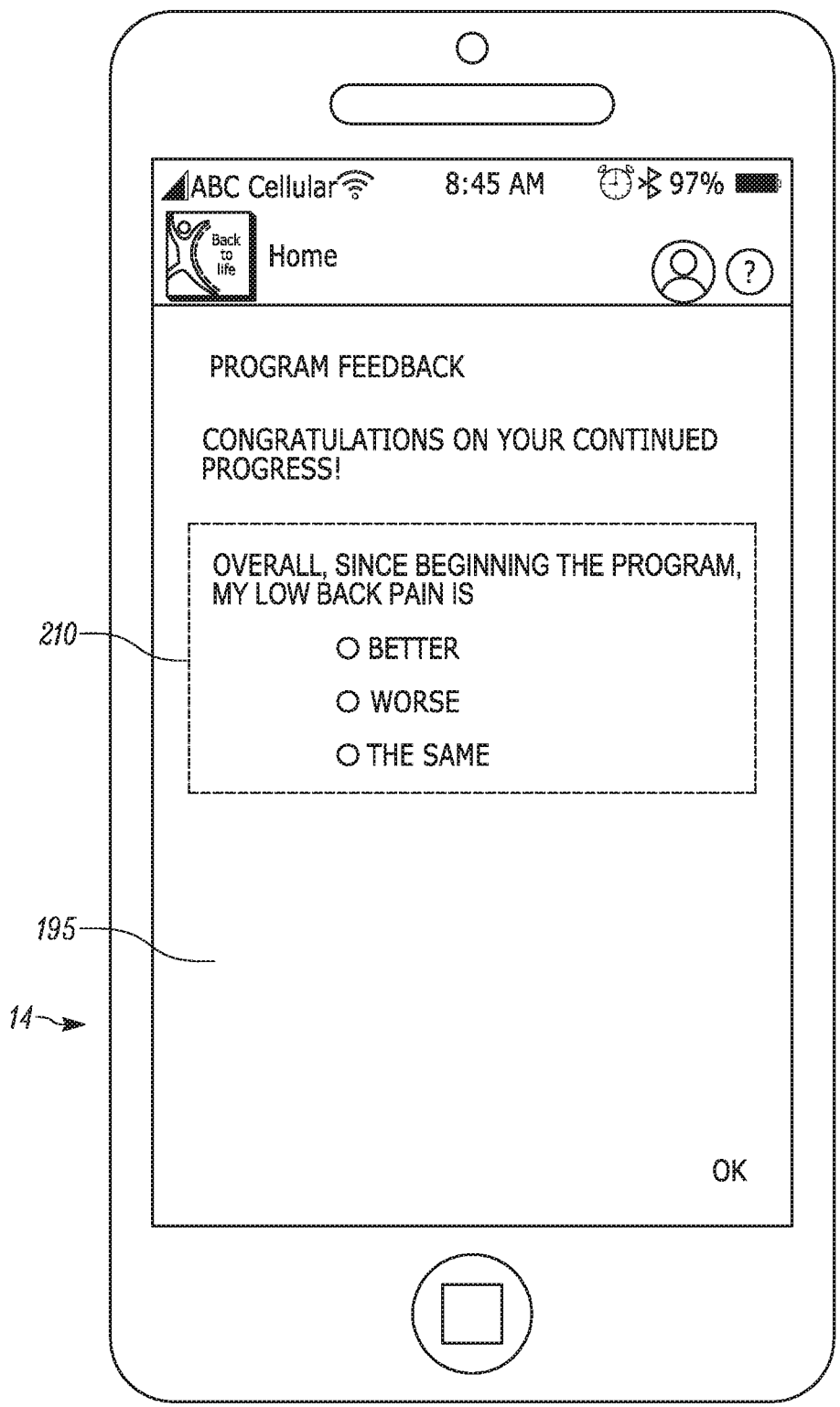
FIG. 15 is a mockup of an exemplary program survey members complete after every $N^{th}$ performance of a routine.

In at least some embodiments, after every $N^{th}$ (e.g., $5^{th}$, $10^{th}$, etc.) performance of the routine, a program survey is also completed by the member 21 to gather the member's perception of the overall impact the health engagement program is having on the condition and a specific functional activity relevant to the member 21. FIG. 15 includes a mockup of an exemplary program survey that includes an overall program impact question 210 for collecting the member's perception.

The information collected by the three exemplary types of surveys (e.g., exercise, routine, and program) is recorded by the mobile application 20 and securely transmitted and stored in one of the databases 41. In addition to responses to exercise, routine, and program surveys completed by members 21, activity, including adherence data, may also be tracked by the mobile application 20 and securely transmitted and stored in one of the databases 41. The reported and recorded data can be utilized by the program application 8 to determine appropriate progression paths for the member 21.

Referring back to FIG. 8, in at least some embodiments, if the program application 8 has not received confirmation that the member 21 has completed the exercises and provided feedback within 72 hours of program initiation or last feedback, then at step 162*a*, a reminder is provided to the member 21 via the mobile application 20 to complete the exercises and provide feedback. Further, in at least some embodiments, after step 162*a*, a timer can be set and if an additional 72 hours transpires without completion of the exercise and feedback, as in step 162*b*, then the member status is flagged yellow and with an "inactivity" trigger, and the administrator 22 is notified. Notification to the administrator 22 invites the administrator 22 to reach out to engage with the member and address the inactivity trigger at step 163 using one or more of various actions, such as referring the member 21 to a specific provider 30 at step 169, sending a stop 170 notification to the member 21 to stop participation in the program, or simply resolving by removing the yellow flag (moving to "green") at step 168.

If the exercise and feedback are determined to be completed at step 164, the process can move to step 165 where the member 21 can optionally request contact from the administrator 22. If contact is requested, then the process moves to step 166 wherein the member 21 is flagged yellow and added to an alert queue, while the administrator 22 is notified. At step 167, the administrator 22 is allowed to take an action on the member's request (e.g., such as utilizing the dashboard application 12 to contact the member 21). After contacting the member 21, the administrator 22 can resolve the request at step 168, refer the member 21 to their specific provider 30 for assistance at step 169, or stop the member 21 from using the program at step 170.

If at step 165, the member 21 does not want contact with the administrator 22, then the process moves to step 171, where the application program 8 runs a progression analysis 298 using the feedback collected in step 164. In at least some embodiments, the progression analysis utilizes data collected through the initial screening process and data collected from exercise, routine, and program surveys completed by members as they perform the assigned exercises, while in other embodiments, the progression analysis can further utilize heuristics gathered from a plurality of experienced professionals who perform associated medical assessments and treatments, along with the collected data. The information and data are processed by the progression analysis performed by the application program 8 to determine when automatic progression to another level of the program is appropriate, when a member 21 should be kept in the current level, when alerts should be triggered, and when a member 21 should be stopped from using the program. Although the progression analysis 298 can vary substantially depending on numerous criteria, as noted above, one exemplary embodiment of the progression analysis is provided in Table 7, along with associated definitions (survey items, database fields, and variables) in Table 6. As should be understood to those skilled in the relevant arts, various modifications can be made to the exemplary progression analysis without diverging from the spirit of the invention, understanding that the progression analysis can include numerous enhancements, substitutions, etc. depending on a particular desired application.

TABLE 6

(multi-part)

Definitions: Survey Items, Database Fields & Variables

| Survey | Survey Item | Definition | Record in DB | Derived Variable | Definition |
|---|---|---|---|---|---|
| SC1-4 | Various | Screening Questions levels 1-4 | All answers | | |
| SC3 | BP | Screening3 Baseline Pain - the initial pain reading recorded to calculate progress throughout the program | 0-10 (whole numbers | • | • |
| N/A | ARA | App Recorded Adherence is the adherence measure calculated by the mobile application, web interface, or other interactive device during exercise performance. | | | |
| ES | PRA | Exercise survey is completed by the member after each exercise Member Reported Adherence is reported by the member as part of the ES to indicate the perceived completion %. | % completion | • | • |
| ES | EE | Exercise survey is completed by the member after each exercise Exercise Effect is the member's perception of the impact the exercise is having on her/his condition | Helping = 1 Hurting = −1 Not changing = 0 No response = Null | • | • |
| RS | | Routine survey is displayed after each routine of exercises Routine is marked Completed if member interacted with 66% (round down) of the exercises in the routine | | RSC | Routine survey Counter - increase by 1 each time Completed RS is received |
| | | | | RSCU | Routine survey Counter Unique - increase by 1 for each RSC increment that occurs on a different calendar day |
| RS | PRP | Routine survey is completed by the member after each routine of exercises Member Reported Pain is the member's perception of her/his current pain level. | 0-10 (whole numbers, same as current) No response = Null | PRPC | PRP Counter - increase by 1 each time PRP received Do not increment if response = Null |

TABLE 6-continued (multi-part)

Definitions: Survey Items, Database Fields & Variables

| Survey | Survey Item | Definition | Record in DB | Derived Variable | Definition |
|---|---|---|---|---|---|
| RS | RE | Routine survey is completed by the member after each routine of exercises Routine Effect is the member's perception of the impact the routine is having on her/his condition | Helping = 1 Hurting = −1 Not changing = 0 No response = Null | REC | RE Counter - increase by 1 each time RE received - Do not increment if response = Null |
| RS | Contact | Routine survey is completed by the member after each routine of exercises Request Contact indicates whether the Member would like to be contacted by a Care Manager or Medical Provider. | Checked = True Not checked = False Note - this is a trigger for a Request Status - it can be triggered multiple times | • | • |
| PS | | Program survey is an overall survey sent to members at defined intervals. Display rule: Displays after RS, after every 5th time response returned to RS (RSC = multiple of 5; i,e. RSC/5 has remainder of 0) | | PSC | Program survey Counter - increase by 1 each time PS received |
| PS | PE | Program survey is an overall survey sent to members at defined intervals. Program Effect is the member's perception of the impact the program is having on her/his condition | Helps = 1 Hurts = −1 No change = 0 No response = Null | PEC | PE Counter - increase by 1 each time PRP received - Do not increment if response = Null |

TABLE 7

Progression Analysis

| | |
|---|---|
| Reset parameters | Reset for each routine GUID per user (i.e., start over when member begins new Level) |
| When run | IF RSC increments, (IF PSC ≥ 2 AND RSCU ≥ 10), THEN run Progression Analysis |
| Formulas | APRP = (Sum PRP)/PRPC Rolling average of last 10 responses in current Level; truncate after tenth's place e.g. 6.4) ΔPRP = APRP − BP (Rolling average of last 10 responses in current Level) ARE = (Sum RE)/REC (Rolling average of last 10 responses in current Level; truncate after tenth's place e.g. 6.4) ARE = (Sum RE)/PEC (Rolling average of last 10 responses in current Level; truncate after tenth's place e.g. 6.4) |

Progression Analysis & Results

IF (APRP ≤ 8 AND ΔPRP < 2 AND ARE ≥ 0 AND APE ≥ 0), PASS
ELSE IF (ARE < −.5 OR APE < −.5), RED
ELSE, ORANGE

The data collected and results of the progression analysis 298 are processed by the application program 8 and used to deliver the resulting care triage and messaging to the member 21. This may include, as determined, one or more actions including: (a) continuing the member in his or her current exercise routine and delivering an appropriate message to the communication device 14 of the member, (b) automatically expiring (i.e. removing) the current exercise routine, or (c) delivering the next level of the routine. More particularly, in at least some embodiments, at step 171, the application program 8 utilizes the progression analysis to determine if a member 21 should progress to a Pass result, an Orange result, or a Red result. If the progression analysis 298 determines a progression to Red, then the process advances to step 173 where the mobile application 20 can inform the member 21 that they are no longer to continue with the program, and should instead see their healthcare provider 30, and their access to the content 45 is revoked. If the progression analysis determines a progression to Orange, then the process advances to step 175 where a message is sent to the member 21 indicating that they are to continue at the current level (and not advance). If the progression analysis determines a progression to Pass, then the process advances to step 178 where a message is sent to the member 21 indicating they have successfully completed the current level and the process advances to step 180.

In step 180, verification of level completion occurs and the member 21 is advanced to the next appropriate level based on the previously completed level. For example, if the member 21 had successfully completed Level 1, then the process advances to step 181, to place the member 21 into Level 2, and the appropriate content for that level is delivered. The member 21 then advances to step 161 to utilize the new content and provide feedback again. If verification of level 2 completion occurs at step 180, then the process advances to step 182 to place the member 21 into Level 3. The member 21 then advances to step 161 to utilize the new content and provide feedback again. Finally, if the member 21 has completed Level 3, the process advances to step 183 and the member is placed in the maintenance level. This process repeats until the member 21 is stopped from the program (e.g., step 170 or 173) or completes all 3 levels and enters maintenance at step 183, which then advances to step 184 sending the member 21 a satisfaction survey to complete.

Figure 16:
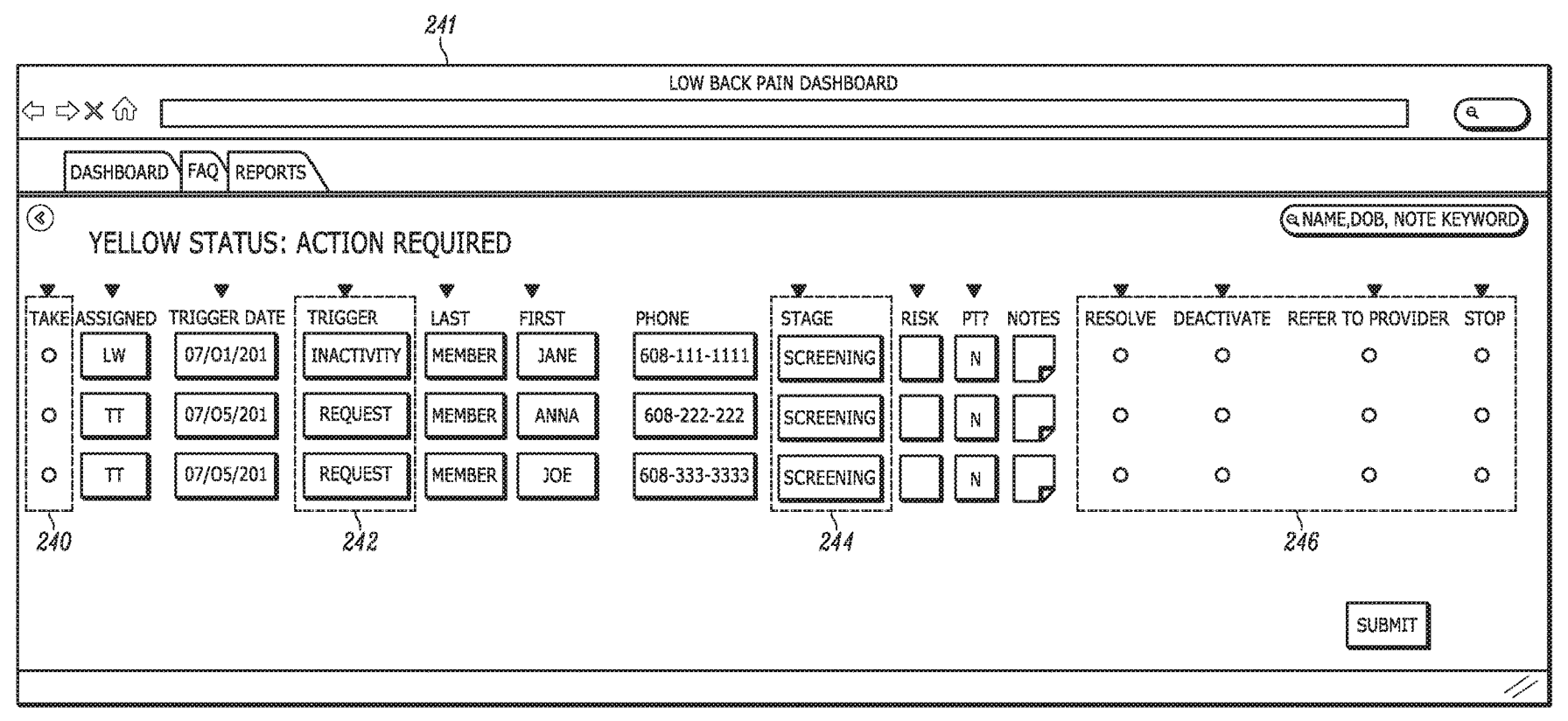

As noted above, the administrator 22 can utilize the dashboard application 12 to perform various functions. For example, FIG. 16 provides a mockup of an exemplary webpage 241 that an administrator 22 can access using a portal 9. As shown, in at least some embodiments, the administrator 22 can: select one of the requests 240 submitted by a member 21 (such as initiated in step 165); determine the trigger 242 that initiated a member's yellow flag status (such as generated in step 166); view the program stage 244 of the member 21 (as identified in step 180); and initiate an appropriate action 246 to resolve an administrator action requirement.

Figure 17:
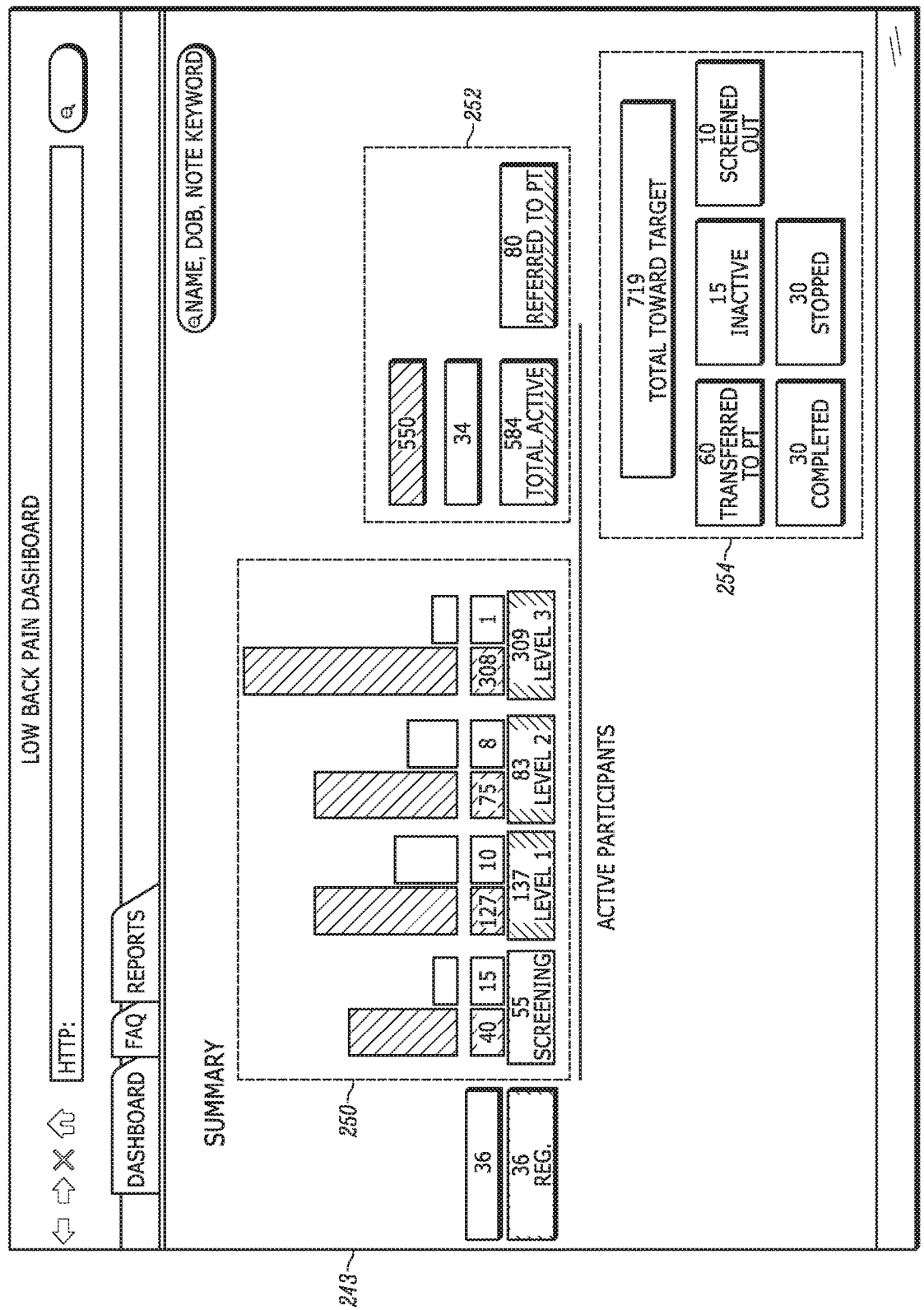
FIG. 17 is a mockup of an exemplary webpage within the dashboard application and utilized by an administrator to monitor member participation and progression, and receive alerts when investigation and/or action may be needed.

FIG. 17 shows a mockup of an exemplary summary webpage 243 accessible by the administrator 22 to review the progress and status of members 21 (e.g., levels, yellow flag status, etc.). The summary webpage displays aggregate totals of members 21 in the various stages of the program 250, such as screening, etc. The summary webpage also indicates totals for all active members 252 and total numbers for all current and past members 254. Using the portal 9 to interface with the dashboard application 12, the administrator 22 can review members 21 that have registered, completed screening, requested contact, progressed to a new level, been stopped from participation, referred to a medical provider, or reached a variety of other standard and customized thresholds. Detailed information about a specific status and totals are available by selecting the corresponding item on the summary screen.

Figure 18:
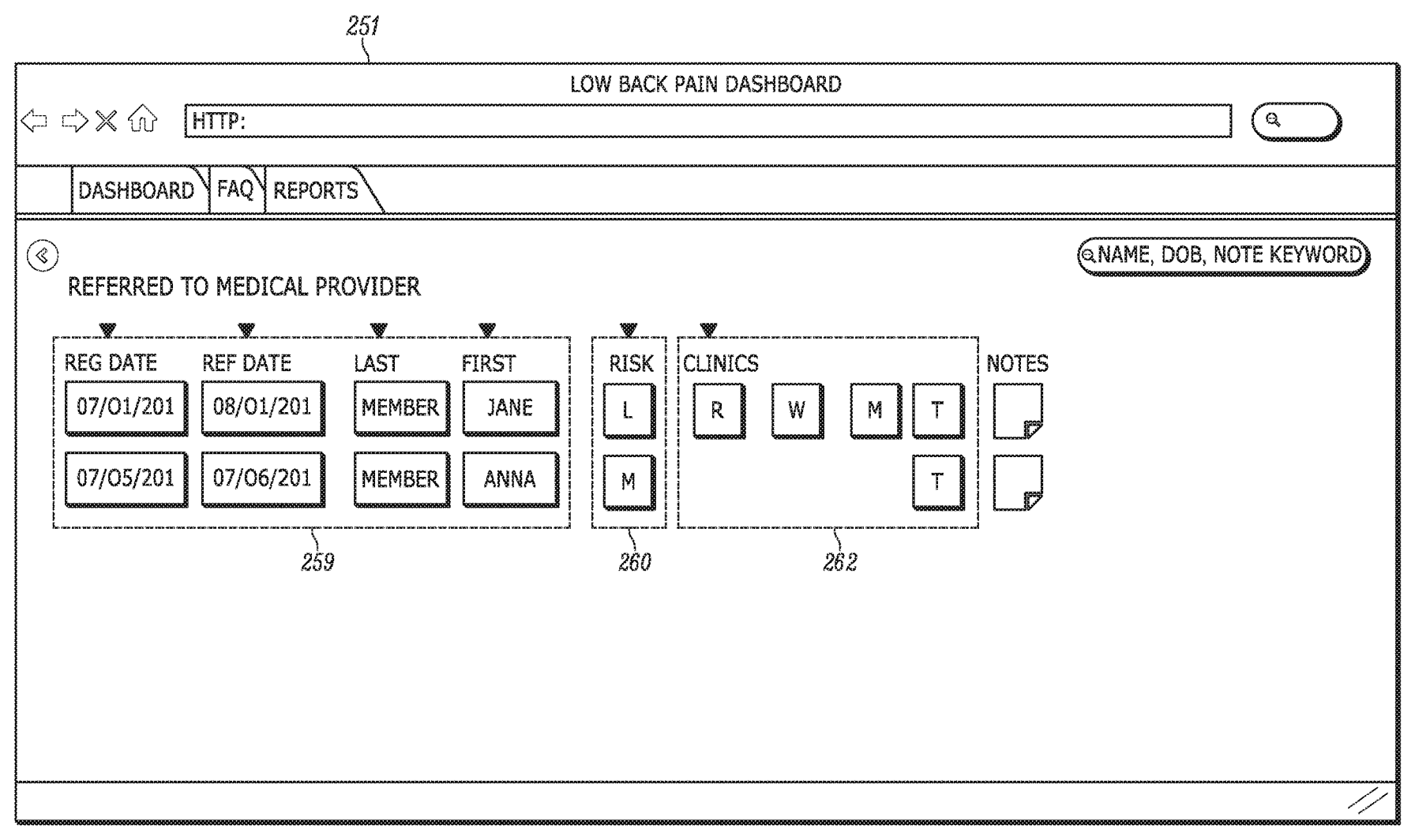

FIG. 18 illustrates a mockup of an exemplary webpage 251 illustrating a member list 259 that includes members 21 referred to a medical provider 30, including the risk level 260 (step 70) identified during screening, as well as the preferred clinics 262 for each member 21. FIG. 19 illustrates a screen shot of an exemplary webpage 261 depicting a "Yellow Flag Disposition" report available to administrators 22 via portal access to the dashboard application 12, the report including the member list 269, the trigger 270 that placed each listed member 21 in yellow flag status, the current stage 272 of the member, the disposition date 274, and the specific disposition of the alert 276.

Figure 20:
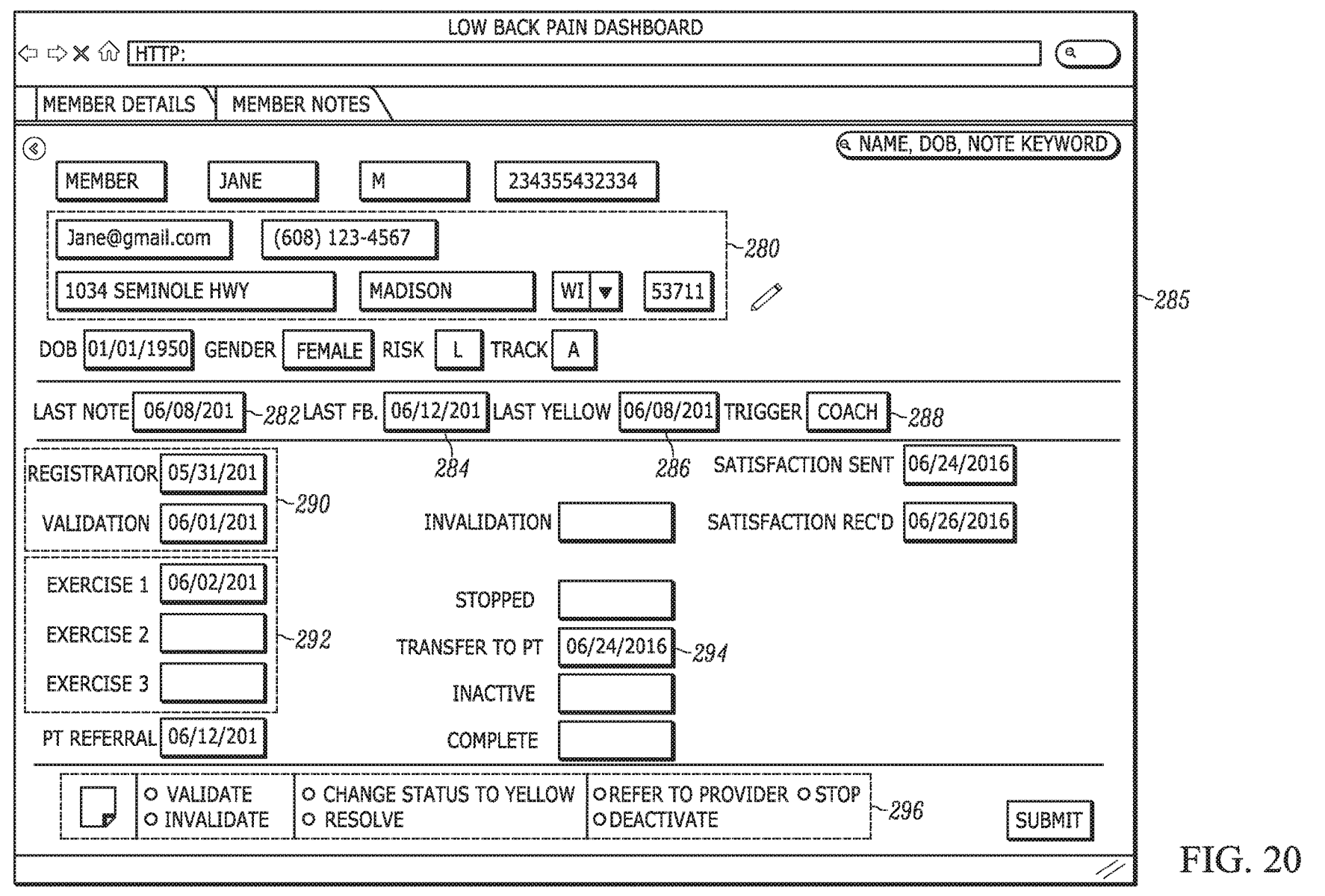

In addition to reviewing summary and reporting information, authorized and appropriate administrators 22 can review and update the details of members 21 by accessing the dashboard application 12. For example, FIG. 20 provides a mockup of an exemplary webpage 285 that includes member details such as contact information 280, which can be updated by the administrator 22. In addition, member progress can be monitored with information such as the last time a note was entered 282, last feedback from member 284, and the date 286 and trigger/cause 288 of the last alert. In this exemplary embodiment, the complete history is also available including registration and validation dates 290, routine distribution dates (by level) 292, transfer date 294, and various other key program dates. Finally, the administrator 22 can initiate actions 296 for a specific member 21 from the exemplary webpage.

Figure 21:
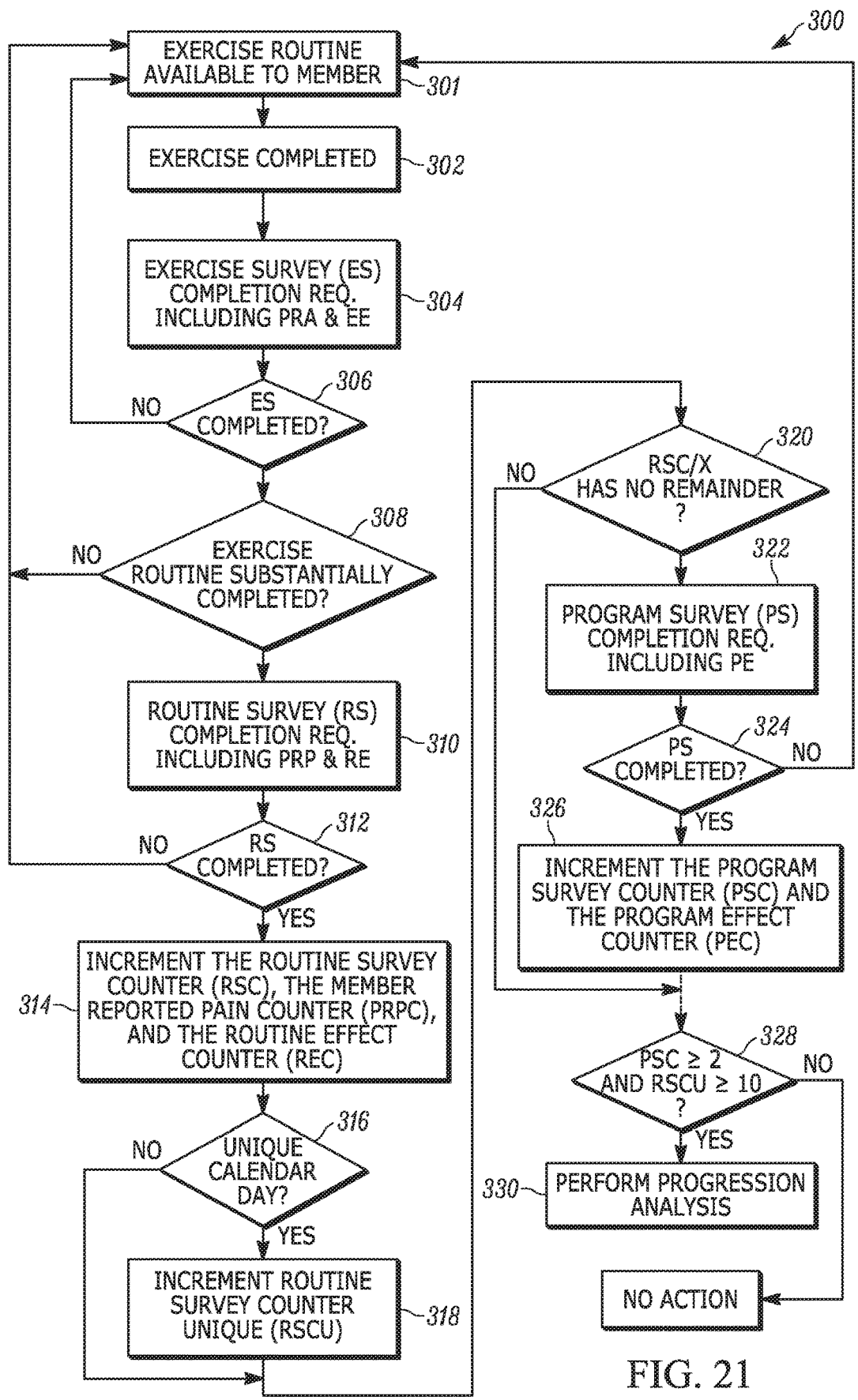
FIG. 21 is a flowchart illustrating exemplary steps to obtain member data and track progression during use of the health engagement program.
Figure 22:
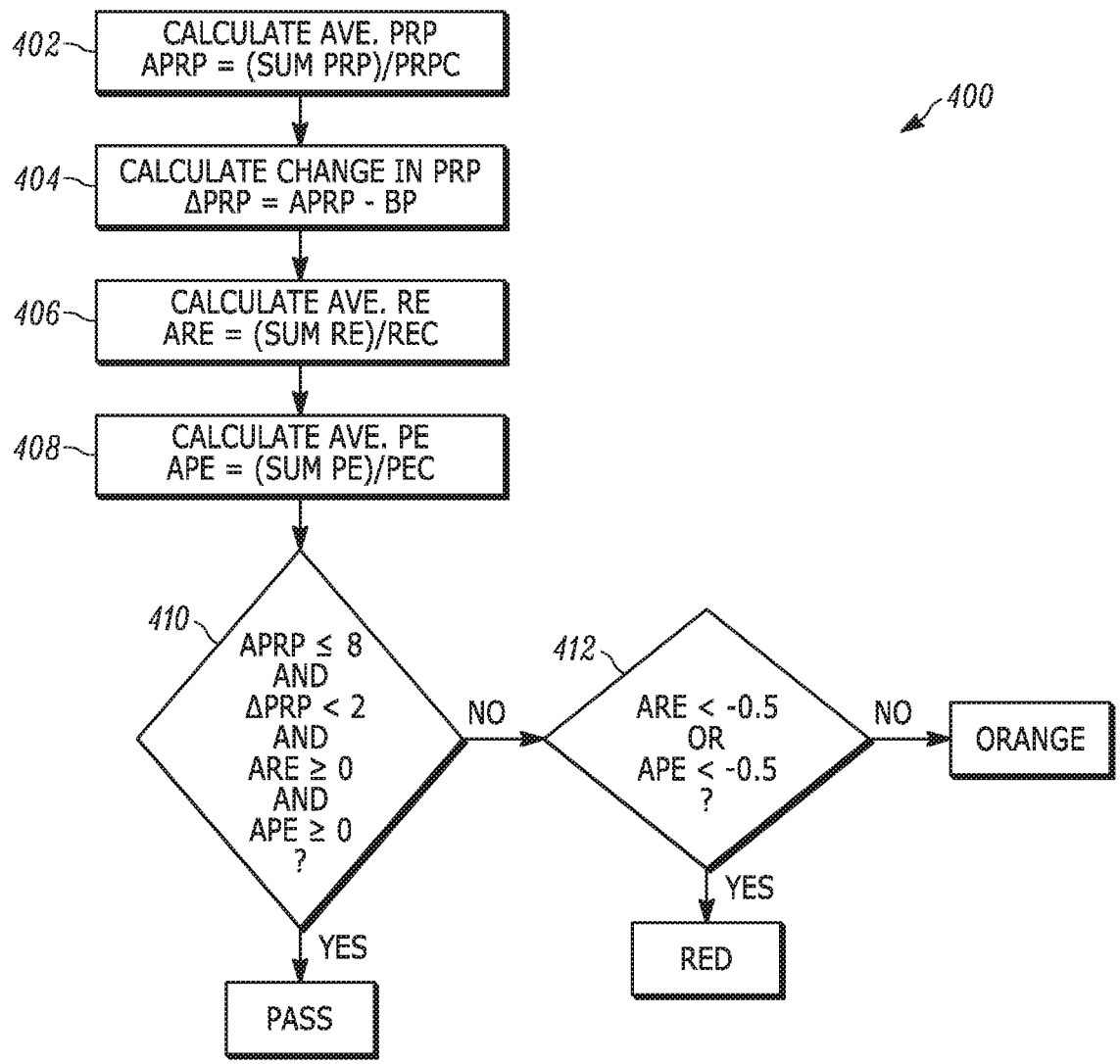
FIG. 22 is a flowchart illustrating an exemplary embodiment of progression analysis.

FIGS. 21 and 22 provide exemplary flowcharts illustrating the progression analysis 298 and associated process steps used to decide when the progression analysis is to be performed, as well as the acquisition and generation of various variables used in the progression analysis. The FIGS. are supplemented by the information disclosed in Tables 6 and 7.

Referring to FIG. 21, a flowchart 300 illustrating steps to track progression and obtain data from the member 21 during their use of the health engagement program is provided. As discussed above, member participation includes receiving an exercise routine on the communication device 14 that includes a plurality of exercises to be performed by the member 21. At step 301 the member has received an exercise routine. Once the member 21 has completed an exercise from the exercise routine at step 302, then at step 304, the application program 8 or the mobile application 20 requests, via display on the communication device 14, completion of the exercise survey (ES), which can include exercise survey queries to obtain, member reported adherence (i.e. perceived exercise completion percentage) (PRA), and member perceived exercise effect (EE) (e.g., helping=1, hurting=−1, no change=0, etc.). At step 306, the application program 8 or the mobile application 20 checks completion of the exercise survey and advances to step 308 if complete. If not complete, then the process can return to step 301 to allow the member 21 to perform the next exercise in the exercise routine, wherein in at least some embodiments, the next exercise in the exercise routine can be automatically presented to the member 21.

At step 308 the application program 8 or the mobile application 20 checks if the member has completed at least a majority (about 66% in some embodiments, more or less in other embodiments (e.g., 51%, 75%, etc.) of the exercises that were provided in the exercise routine, if so the process advances to step 310, if not the process returns to step 301. At step 310 the application program 8 or the mobile application 20 requests, via display on the communication device 14, completion of the routine survey (RS), which can include routine survey queries to obtain, values for member reported pain (PRP) (e.g., chosen from a scale of 1-10), and routine effect (RE) reflecting the member's perceived impact of the routine on the condition (e.g., helping=1, hurting=−1, no change=0, etc.). At step 312 the application program 8 or the mobile application 20 checks completion of the routine survey and if complete, advances to step 314 to increment the routine survey counter (RSC), the member reported pain counter (PRPC), and the routine effect counter (REC), and if not complete returns to step 301.

If the routine survey counter is incremented, then at step 316 the application program 8 or the mobile application 20 checks if the calendar date associated with the routine survey counter incrementation is unique to prior calendar dates recorded with routine survey counter incrementation, if not unique, the process moves to step 320, and if unique, then at step 318 the routine survey counter unique (RSCU) value is incremented before advancing the process to step 320. The RSCU counter is used to differentiate when a member has completed numerous exercise routines on the same day. In at least some embodiments, it is desired that the member complete at least ten exercise routines on ten unique days before a progression analysis is performed, while in other embodiments, other quantities of completion can be utilized.

At step 320, the application program 8 or the mobile application 20 divides the RSC value by a pre-chosen value "X" (e.g., $N^{th}$, 5, 10, etc.) that represents a desired number of completed routine surveys before a program survey is requested. If the reminder of the division is not zero, the process advances to step 328, and if the reminder is zero, then it is known that the RSC value has reached a desired quantity and the process advances to step 322, where the application program 8 or the mobile application 20 requests, via display on the communication device 14, completion of the program survey (PS), which can include program survey queries such as, requesting a value for program effect (PE) that reflects the member's perceived impact of the program on the condition (e.g., helping=1, hurting=−1, no change=0, etc.). At step 324 the application program 8 checks for completion of the program survey and advances to step 326 to increment the program survey counter (PSC) and program effect counter (PEC) if complete, or returns to step 301 if not complete. At step 328, the application program 8 checks if both the stored PSC value is ≥2 and the stored RSCU value is ≥10, and if so, then the application program preforms the progression analysis at step 330. It shall be understood that all values obtained and calculated during the described process can be stored in one or more of the databases 41. Although in the flowchart the various steps are shown progressively, in at least some embodiments, various steps are performed by the application program 8 independent of any action taken or data received from the member's communication device 14. More particularly, and by example, at least steps 328 and 330 can occur on the server 4 independent of any communication occurring between the server and the member's communication device 14. To this end, it shall be understood that various steps can be run at different times and with different frequencies relative to other steps and performed by different devices.

Referring now to FIG. 22, flowchart 400 illustrates one embodiment of the progression analysis 298 that can be performed following step 330 of flowchart 300. In at least some embodiments, the progression analysis 298 is performed using the latest values obtained and/or calculated by the application program 8, therefore, when data values used in the progression algorithm 298 exceed a desired quantity, the application program 8 can be configured to utilize only the most recent values (e.g., the ten most recent values), while in other embodiments, all stored values can be utilized.

Beginning at step 402, the application program 8 calculates the average member reported pain (APRP), which includes dividing the sum of the PRP values by the PRPC value, noting that in at least some embodiments, the PRP values include the ten most recent PRP values (although less or more PRP values can be utilized in other embodiments), which allows the APRP to provide a rolling average value. Advancing to step 404, the application program 8 calculates the change in member reported pain (ΔPRP), which include subtracting the baseline pain (BP) from the APRP value. It is noted that the BP is a value received from the member 21 in response to a screening-based query, which queried the member 21 to input a value (e.g., chosen from a scale of 1-10) representing their initial pain level. Advancing to step 406, the application program 8 calculates the average routine effect (ARE), which includes dividing the sum of the RE values by the REC value, noting that in at least some embodiments, the RE values include the ten most recent RE values, which allows the ARE to provide a rolling average value. Advancing to step 408, the application program 8 calculates the average program effect (APE), which includes dividing the sum of the PE values by the PEC value, noting that in at least some embodiments, the PE values include the ten most recent PE values, which allows the APE to provide a rolling average value.

Advancing to step 410, the application program 8 evaluates the values to determine if the following are all true: APRP≤8, and ΔPRP<2, and ARE≥0, and APE≥0, if true, then the application program 8 provides a Pass indication (see steps 171 and 178 in flowchart 158 of FIG. 8) allowing the member 21 to advance to the next level (whenever a Pass indication occurs, the PSC and RSCU are reset to zero). If not true, then the process advances to step 412, where the application program 8 evaluates the values to determine if either of the following are true: ARE<−0.5 and APE<−0.5, if either true, then the application program 8 provides a Red indication (see steps 171 and 173 in flowchart 158 of FIG. 8), and if both false, then the application program 8 provides an Orange indication (see steps 171 and 175 in flowchart 158 of FIG. 8). It shall be understood that in at least some embodiments, the values used for comparison in steps 410 and 412 (8, 2, 0, −0.5, etc.) can vary to be higher or lower, depending on desired criteria. Criteria for choosing other values can include heuristics gathered from a plurality of experienced professionals who perform associated medical assessments and treatments. As such, the exemplary values provided herein for use in the various aforementioned processes, shall not be construed to be limiting. In addition, the progression algorithm 298 can be executed on a scheduled time basis by the application program 8 and therefore independent of the receipt of new communications from the member's communication device 14, or it can be executed based on specific criteria identified by the application program 8, such as the receipt of a designated communication from the member's communication device or an administrator's communication device.

As described, phase 1 can be completed using a web browser on a communication device to communicate with the application program, which can include web-based registration and screening applications. In at least some embodiments, phase 1 can also be completed using a mobile application or specific resident program that interfaces with the application program. Likewise, in at least some embodiments, phase 2 can also be performed using a web browser instead of or in addition to a mobile application to interface the member with the care delivery application.

It shall be understood that the specific selection of exercises and other criteria throughout is exemplary and can be adapted to address specific goals based on the administrators and members. As such, the use of specific criteria, such as track, risk, yellow and red flags, etc. are exemplary of various identifiers that can be used to determine acceptance and progression in a health management program. In addition, the use of color nomenclature, such as "yellow", "red", "orange", etc. is intended to be exemplary and serves only to classify or otherwise differentiate various conditions for ease of understanding, and as such, other colors or indicia (e.g., numbers, names, letters, etc.) can be utilized to perform the same function as well and shall be considered within the scope of the invention.

In at least some embodiments, data gathered within the databases from the members is consolidated and processed to model additional analyses for estimating recovery time and anticipated improvement in pain scores for members based on screening responses and demographic factors. In further embodiments, the resulting estimated recovery time and anticipated pain score improvement for each member is presented (and updated) through the mobile application or web interface on the member's communication device to provide feedback and motivate each member. In still further embodiments, the estimated recovery time and anticipated pain score improvement for the members can be de-identified, analyzed, consolidated, and presented to the administrator through interactive portals to utilize in setting expectations, monitoring progress, evaluating the efficacy of the program, comparing across populations in peer programs, and identifying potential program modifications for future members.

In at least some embodiments, the mobile application 20 as well as the application program 8, in whole or in part, including the registration application 10, the screening application 11, dashboard application 12, and care delivery application 13, can be fixed in one or more non-transitory computer-readable mediums. Further, in at least some embodiments, mobile application 20 as well as the application program 8 in whole or in part, can be fixed in non-transitory computer readable mediums, wherein the non-transitory computer-readable mediums comprise all computer-readable mediums except for a transitory, propagating signal. Additionally, in at least some embodiments, all or some of the signals generated and received by the application program 8 can include computer-readable signals.

Following from the above description and invention summaries, it should be apparent to those of ordinary skill in the art that, while the systems and processes herein described constitute exemplary embodiments of the present invention, it is to be understood that the invention is not limited to these precise systems and processes and that changes may be made therein without departing from the scope of the invention as defined by the claims. Additionally, it is to be understood that the invention can be defined by the claims and it is not intended that any limitations or elements describing the exemplary embodiments set forth herein are to be incorporated into the meaning of the claims unless such limitations or elements are explicitly listed in the claims. Likewise, it is to be understood that it is not necessary to meet any or all the identified advantages or objects of the invention disclosed herein to fall within the scope of any claims, since the invention is defined by the claims and since inherent and/or unforeseen advantages of the present invention may exist even though they may not have been explicitly discussed herein. The term "plurality" shall be understood to include one or more. The exemplary flowcharts provided herein illustrate one embodiment of the process, although it shall be understood that process can include additional steps and/or omit some steps, as well as execute the steps in a different order.

What is claimed:

1. A system for managing participation and progression in a health engagement program comprising:

a server having a processor, an operating system, a storage device, and an application program that includes a registration application and a screening application;

a network in communication with the server, one or more databases, and a first communication device;

wherein the registration application and screening application are both accessible by the first communication device via one or more portals over the network, and wherein the registration application communicates a plurality of registration-based queries to the first communication device and receives registration-based query responses inputted to the first communication device by a member;

wherein the received registration-based query responses include member information that is compared by the registration application to a listing of eligible member information on the one or more databases to determine participation eligibility of the member in the health engagement program, and wherein confirmation of eligibility generates the communication of a plurality of screening-based queries to the first communication device by the screening application, and wherein non-confirmation of eligibility by the registration application initiates a manual validation request communicated to a second communication device operable by an administrator, wherein receipt by the registration application of a manual validation by an administrator generates communication of the plurality of screening-based queries to the first communication device by the screening application;

wherein screening-based query responses to the screening-based queries are analyzed by the application program to select one of a plurality of exercise tracks and one of a plurality of risk categories associated with the health engagement program;

wherein an associated exercise routine is selected by the application program based on the screening-based query responses, the selected exercise track, and the selected risk category, and communicated to the first communication device by the application program for viewing by the member;

wherein exercise survey feedback is requested from the member upon completion of an exercise from the exercise routine;

wherein routine survey feedback is requested from the member upon substantial completion of all exercises from the exercise routine;

wherein program survey feedback is requested from the member; and wherein the application program executes a progression analysis to determine if the member is to one of: i) be advanced to a subsequent level to receive access to an additional associated exercise routine; ii) remain at the current level and repeat the current exercise routine; or iii) be stopped from further participation.

2. The system of claim 1, wherein the screening-based query responses to the screening-based queries are further analyzed by the application program to identify the existence of a medical red flag.

3. The system of claim 2, wherein identification of at least one medical red flag initiates a notification communication to the administrator; and wherein when a medical red flag has been identified, the member is provided an option to request that the administrator override the medical red flag and allow communication of the selected exercise routine to the first communication device.

4. The system of claim 3, wherein the application program includes a dashboard application in communication with the second communication device, and wherein the dashboard application provides selections for the administrator to manually validate the member or override the at least one medical red flag.

5. The system of claim 4, wherein the risk categories include a high risk category, a medium risk category, and a low risk category.

6. The system of claim 1, wherein the one or more databases receive and store the registration-based query responses, the screening-based query responses, the exercise survey feedback, routine survey feedback, and the program survey feedback.

7. The system of claim 1, wherein the first communication device includes at least one of a web browser and a mobile application for communicating with the application program.

8. A computerized process for managing member participation and progression in a health engagement program comprising:
    communicating over a network, a plurality of registration-based queries from a server to a first communication device;
    receiving from the first communication device, registration-based query responses inputted by a member using the first communication device, wherein the registration-based query responses include member identification data;
    determining health engagement program participation eligibility of the member by comparing at least a portion of the member identification data with a list of eligible member identification data stored in one or more databases in communication with the server, wherein confirmation of member eligibility initiates the communication of a plurality of screening-based queries to the first communication device, and wherein a lack of confirmation of eligibility during the comparison initiates communication to a second communication device, operable by an administrator, of a request for a manual validation, and wherein receipt of the manual validation by the administrator the plurality of screening-based queries is communicated to the first communication device;
    receiving screening-based query responses from the first communication device;
    analyzing the screening-based query responses and selecting one of a plurality of exercise tracks and one of a plurality of risk categories associated with the health engagement program;
    selecting an associated exercise routine based on the screening-based query responses, the selected exercise track, and the selected risk category;
    communicating the exercise routine to the first communication device for viewing by the member thereon;
    receiving a selection by the member to view the exercise routine;
    upon completion of the exercise routine, communicating a request to the first communication device for the member to provide survey feedback, wherein the survey feedback includes a plurality of survey questions presented to the member; and
    analyzing the responses to the survey feedback and determining if the member shall, i) progress to a subsequent level in the program, thereby receiving access to a new exercise routine, ii) remain at the current level, thereby repeating the current exercise routine, or iii) be stopped from further participation by revocation of the member's access to the exercise routine.

9. The process of claim 8, further including analyzing the screening-based query responses to identify the existence of a medical red flag, and if identified, then preventing member access to the selected exercise routine and communicating notification of the medical red flag to the administrator; wherein if an administrator override for the medical red flag is received, then allow communication of the selected exercise routine to the first communication device.

10. The process of claim 9, wherein the application program includes a dashboard application in communication with the second communication device, and wherein the dashboard application provides selections for the administrator to provide the administrator override.

11. The process of claim 10, wherein the dashboard application provides the administrator access to a plurality of data stored on the one or more databases, including subtotals of members that have, completed registration-based queries, completed screening-based queries, requested contact from an administrator, advanced to a new level, and been stopped from further participation.

12. The process of claim 8, wherein selecting one of the plurality of risk categories includes selecting one of a high risk category, a medium risk category, and a low risk category.

13. The process of claim 12, wherein selecting the exercise routine includes selecting one of three types of exercise tracks, comprising an extension track, a flexion track, and a non-directional track.

14. A computerized process for managing member participation and progression in a health engagement program comprising:
    requesting and receiving member identification information from a member communicated between a server and a first communication device operated by the member;
    comparing at the server, the member identification information to a list of known eligible members in one or more databases and automatically validating eligible members to participate in the health engagement program if provided on the list, and queuing members not on the list for manual review and validation;
    providing an interactive portal in communication with the server to enable an administrator using a second communication device to manually validate or invalidate queued members not on the list;
    after validation, requesting and receiving a plurality of screening-based query responses from the member, wherein the screening-based query responses are directed to a medical condition experienced by the member, activities that aggravate the condition, and the member's medical history;

analyzing the screening-based query responses and stratifying the member into a selected exercise track and risk category based on the disclosed condition, activities that aggravate the condition, and the member's medical history;

selecting an associated exercise routine from a plurality of exercise routines based on the screening-based query responses, the selected exercise track, and the selected risk category; and providing the member access to view the exercise routine through a mobile application or web browser operating on the first communication device.

15. The process of claim 14, wherein the exercise routine accessible to the member includes a plurality of exercises demonstrated by at least one of an animation depicting a representative human rendering performing each exercise and a video of a human performing each exercise.

16. The process of claim 15 further comprising, providing the member with a selection to view an abbreviated or a non-abbreviated version of the exercise routine.

17. The process of claim 16 further comprising, providing the member access to view education material related to the condition using the mobile application or web browser.

18. The process of claim 15, further comprising providing an exercise survey to the member requesting exercise survey feedback at the completion of each exercise in the exercise routine.

19. The process of claim 18, further comprising providing a routine survey to the member requesting routine survey feedback at the completion of a majority of the exercises in the exercise routine.

20. The process of claim 19, further comprising identifying the completion or non-completion of the routine survey, and if completion is identified, incrementing a routine survey counter value.

21. The process of claim 20, further comprising comparing the calendar date of the routine survey counter incrementation with calendar dates of prior routine survey counter incrementation and if unique, then incrementing a routine survey counter unique value.

22. The process of claim 21, further comprising providing a program survey to the member requesting program survey feedback.

23. The process of claim 22, further comprising performing a progression analysis to determine if the member should progress to a subsequent level thereby receiving access to a subsequent exercise routine.

24. The process of claim 22, further comprising:
wherein a baseline pain value, a plurality of member reported pain values, a plurality of routine effect values and a plurality of program effect values are received from the member and stored in the one or more databases;
wherein values for a program survey counter, a routine survey counter, a member reported pain counter, and a program effect counter are stored in the one or more databases;
wherein an average member reported pain value is calculated by dividing a sum of member reported pain values by the member reported pain counter;
wherein a change in member reported pain value is calculated by subtracting the baseline pain value from the member reported pain value;
wherein an average routine effect value is calculated by dividing a sum of member reported routine effect values by the routine effect counter;
wherein an average program effect value is calculated by dividing a sum of member reported program effect values by the program effect counter; and
wherein the average member reported pain value, the change in member reported pain value, average routine effect value, and average program effect value are stored in the one or more databases.

25. The process of claim 24, further comprising determining if the average member reported pain value is less than a first pre-determined value, and the change in member reported pain value is less than a second pre-determined value, and the average routine effect value is greater than or equal to zero, and the average program effect value is greater than or equal to zero, and if all true, then providing a pass indication allowing the member to progress to a subsequent level and receive access to an associated subsequent exercise routine, and if not all true, then determining if either the average routine effect value is less than a third pre-determined value or the average program effect value is less than a fourth pre-determined value, and if so, revoking the member's access to the exercise routine, and if not, then allowing the member to continue at a current level and access the exercise routine.

26. The process of claim 25, wherein the selected risk category includes one of a high risk category, a medium risk category, and a low risk category.

27. The process of claim 26, wherein selected exercise track includes one of, an extension track, a flexion track, and a non-directional track.

28. A computerized process for managing member participation and progression in a health engagement program, comprising the steps of:
for a plurality of members, gathering member identification information with the assistance of a plurality of communication devices and a server;
for the plurality of members, comparing the member identification information to a list of eligible members in one or more databases to automatically validate eligible members found in the list and allow them to continue as validated members in the health engagement program;
queuing for manual review and validation, the plurality of members not automatically validated, and providing an interactive portal to enable an administrator to manually validate for participation in the health engagement program, wherein the interactive portal is in communication with the server;
for the validated members, gathering with the assistance of a communication device in communication with the server, member screening information that includes access to equipment required for the health engagement program, and at least one medical factor associated with each member's health history, taken from a group consisting of (a) type of condition, (b) relevant comorbidities (c) current pain level, (d) highest level of pain over a certain period, (e) activities that aggravate the condition, and (f) activities of daily living affected by the condition;
stratifying, with the assistance of an application program in communication with the server, each of the validated members into risk categories based on the screening information gathered; and
with the assistance of the application program, determining whether each validated member is appropriate for and suitable to continue with the health engagement program, and flagging, if deemed appropriate, each of the validated members indicating conditions for participation by analyzing the screening information gathered.

29. The process of claim 28, further comprising the step of displaying and categorizing flagged validated members on the interactive portal to allow the administrator to manually override the flags and thereby allow members to continue with the health engagement program.

30. The process of claim 29, further comprising the steps of:
for each validated member, determining the appropriate exercise track based on the gathered medical factors, including at least the type of condition, and the activities that aggravate the condition; and
for each validated member, providing access through a mobile application to an exercise routine selected based on the member screening information.

31. The process of claim 30, wherein the exercise track and the exercise routine are based upon heuristics gathered from a plurality of experienced professionals who perform associated medical assessments and treatments.

32. The process of claim 31, further comprising the step of displaying the exercise routines on the communication device.

33. The process of claim 32, further comprising the step of providing the member an option to select an abbreviated or non-abbreviated variation of the exercise routine within the mobile application.

34. The process of claim 33, further comprising the step of recording the selected variation in the one or more databases for analysis along with other data recorded during the routine performance.

35. The process of claim 32, further comprising the steps of:
for each validated member, with the assistance of the mobile application, recording data including exercises performed, performance duration, and completion percentage during each performance of the exercise routine, wherein the data is stored in the one or more databases;
for each validated member, with the assistance of the mobile application, gathering member perceptions after each exercise performance including perceived completion percentage, and perceived impact on their condition; and
for each validated member, with the assistance of the mobile application, gathering member perceptions after each routine performance including perceived pain and how the exercise routine is impacting the condition.

36. The process of claim 35, further comprising the step of:
for each validated member, with the assistance of the mobile application, after repeated performances of the exercise routine, gathering member perceptions of the overall impact the health engagement program is having on the condition.

37. The process of claim 36, further comprising the steps of:
for each validated member, with the assistance of the mobile application, collecting requests for the administrator to contact the member and flagging the member when such a request is submitted; and
flagging members requesting contact in the interactive portal and providing a mechanism within the interactive portal for the administrator to remove the flag after completing the requested contact.

38. The process of claim 36, further comprising the steps of:
for the validated members, with the assistance of the application program utilizing a progression analysis, processing the gathered data to determine if the members should proceed to the next level of the exercise treatment program or remain in the current level;
for each of the validated members that should proceed to the next level of the health engagement program, remove the current exercise routine from the mobile application and allow access to a subsequent appropriate exercise routine for the next level; and
for each of the validated members that should proceed to the next level of the exercise treatment program, deliver to the mobile application an appropriate progress message.

39. The process of claim 38, wherein level progression and exercise routine selection are based upon heuristics gathered from a plurality of experienced professionals who perform associated medical assessments and treatments.

40. The process of claim 39, further comprising the step of enabling the administrator to update the details of members and take actions to manage members in the health engagement program including updates to member information, manual validation, resetting member flag status, and overriding flags to allow members to continue in the health engagement program.

41. The process of claim 40 further comprising the step of enabling the administrator to take action to refer members to medical providers, de-activate participation in the health engagement program due to disinterest or inactivity, or to stop members from participation in the health engagement program due to medical reasons.

* * * * *